US009861105B2

(12) United States Patent
Huang et al.

(10) Patent No.: US 9,861,105 B2
(45) Date of Patent: Jan. 9, 2018

(54) METHODS AND COMPOSITIONS FOR CONTROLLING NEMATODE PESTS

(75) Inventors: Xiang Huang, Research Triangle Park, NC (US); Jeng Shong Chen, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 528 days.

(21) Appl. No.: 14/232,967

(22) PCT Filed: Jul. 11, 2012

(86) PCT No.: PCT/US2012/046239
§ 371 (c)(1),
(2), (4) Date: Mar. 10, 2014

(87) PCT Pub. No.: WO2013/015993
PCT Pub. Date: Jan. 31, 2013

(65) Prior Publication Data
US 2014/0296138 A1 Oct. 2, 2014

Related U.S. Application Data

(60) Provisional application No. 61/512,575, filed on Jul. 28, 2011.

(51) Int. Cl.
*C12N 15/82* (2006.01)
*A01N 65/20* (2009.01)
*A01N 37/46* (2006.01)
*A01N 37/44* (2006.01)

(52) U.S. Cl.
CPC ............ *A01N 65/20* (2013.01); *A01N 37/44* (2013.01); *A01N 37/46* (2013.01); *C12N 15/8261* (2013.01); *C12N 15/8285* (2013.01)

(58) Field of Classification Search
None
See application file for complete search history.

(56) References Cited

U.S. PATENT DOCUMENTS

| | | | |
|---|---|---|---|
| 5,770,696 A | 6/1998 | Warren et al. | |
| 5,840,868 A | 11/1998 | Warren et al. | |
| 5,866,326 A | 2/1999 | Warren et al. | |
| 5,872,212 A | 2/1999 | Warren et al. | |
| 5,877,012 A | 3/1999 | Estruch et al. | |
| 5,877,102 A | 3/1999 | DuPont et al. | |
| 5,888,801 A | 3/1999 | Warren et al. | |
| 5,889,174 A | 3/1999 | Warren et al. | |
| 5,990,383 A | 11/1999 | Warren et al. | |
| 6,066,783 A | 5/2000 | Warren et al. | |
| 6,107,279 A | 8/2000 | Estruch et al. | |
| 6,137,033 A | 10/2000 | Estruch et al. | |
| 6,291,156 B1 | 9/2001 | Estruch et al. | |
| 6,429,360 B1 | 8/2002 | Estruch et al. | |
| 7,071,391 B1* | 7/2006 | Threlkeld ............... | A01H 5/10 435/415 |
| 7,244,820 B2 | 7/2007 | Miles et al. | |
| 7,304,217 B1* | 12/2007 | Bowers .................... | A01H 5/10 435/415 |
| 7,615,686 B2 | 11/2009 | Miles et al. | |
| 8,232,456 B2 | 7/2012 | Long et al. | |
| 8,237,020 B2 | 8/2012 | Miles et al. | |
| 8,455,720 B2 | 6/2013 | Long et al. | |
| 8,598,117 B2 | 12/2013 | Miles et al. | |
| 8,618,272 B2 | 12/2013 | Long et al. | |
| 8,686,232 B2 | 4/2014 | Shen et al. | |
| 2004/0128716 A1 | 7/2004 | Narva et al. | |
| 2006/0130175 A1* | 6/2006 | Ellis ................... | C12N 15/8286 800/279 |
| 2008/0256669 A1* | 10/2008 | Fabbri ................ | C12N 15/8261 800/300.1 |
| 2009/0300784 A1* | 12/2009 | Long .................... | C07K 14/415 800/265 |
| 2013/0097728 A1* | 4/2013 | Heinrichs .......... | C12N 15/8286 800/279 |

FOREIGN PATENT DOCUMENTS

| | | | | |
|---|---|---|---|---|
| ES | WO 2009132850 A1 * | 11/2009 | ......... C12N 15/8286 | |
| WO | 9421795 | 9/1994 | | |
| WO | 9610083 | 4/1996 | | |
| WO | 9800546 | 1/1998 | | |
| WO | 9818932 | 5/1998 | | |
| WO | 9844137 | 10/1998 | | |
| WO | 9957282 | 11/1999 | | |
| WO | 02078437 | 10/2002 | | |
| WO | 03075655 | 9/2003 | | |
| WO | 2007142840 | 12/2007 | | |
| WO | WO 2007142840 A2 * | 12/2007 | ........... C07K 14/415 | |
| WO | 2013022720 | 2/2013 | | |

OTHER PUBLICATIONS

Fourgoux-Nicol et al (1999, Plant Molecular Biology 40: 857-872).*
Davolos et al, cry1 genes from Bacillus thuringiensis: specificity determination and implications for primer design. Biotechnol Lett 31:1891-1897, 2009.*
Phap et al (Engineering Resistance in Brinjal against Nematode (Meloidogyne Incognita) Using cry1 Ab Gene from Bacillus Thuringiensis Berliner. IFMBE Proceedings vol. 27: 278-281, 2010).*
Chung et al (GenBank: DQ005476.1, public available on Aug. 16, 2005).*
Friedberg (Automated protein function prediction—the genomic challenge. Brief. Bioinformatics. 7:225-242, 2006).*

(Continued)

*Primary Examiner* — Medina A Ibrahim
*Assistant Examiner* — Wayne Zhong
(74) *Attorney, Agent, or Firm* — Christopher L. Leming

(57) ABSTRACT

Transgenic plants expressing a Vip3 protein have been found to be efficacious against plant-infesting nematodes. Disclosed are methods of controlling nematode populations using transgenic plants expressing Vip3 protein.

12 Claims, No Drawings

(56) References Cited

OTHER PUBLICATIONS

Fourgoux-Nicol et al (Isolation of rapeseed genes expressed early and specifically during development of the male gametophyte, Plant Molecular Biology 40: 857-872, 1999).*

Mohammed et al (Evaluation of Potato Tuber Moth (Lepidoptera: Gelechiidae) Resistance in Tubers of Bt-cry5 Transgenic Potato Lines. Journal of Economic Entomology, 93(2):472-476, 2000).*

Bravo et al (Mode of action of Bacillus thuringiensis Cry and Cyt toxins and their potential for insect control. Toxicon. 49(4): 423-435, Mar. 2007).*

Estruch et al., "VIP3A, a novel bacillus thuringiensis vegetative insecticidal protein with a wide spectrum of activities against lepidopteran insects," Proceedings of the National Academy of Sciences, National Academy of Sciences, US, vol. 93, May 1, 1996, pp. 5389-5394.

International Search Report/Written Opinion for International Patent Application No. PCT/US2012/046239 dated Jan. 11, 2013.

L. Palma, et al., "Bacillus thuringiensis Toxins: An Overview of Their Biocidal Activity," Toxins, vol. 6, pp. 3296-3325, Dec. 11, 2014.

L.A. Mesrati, et al., "Characterization of a novel vip3-type gene from Bacillus thuringiensis and evidence of its presence on a large plasmid," FEMS Microbiology Letters, Issue 224, pp. 353-358, Feb. 14, 2005.

Phillip McClean, "Nucleic Acid Hybridizations", DNA—Basics of Structure and Analysis, 1998, http://www.ndsu.edu/pubweb/~mcclean/plsc731/dna/dna6.htm , last visited May 25, 2016.

"Bacillus Thuringiensis Toxins: An Overveiw of Their Biocidal Activity", Toxins 2014, vol. 6, pp. 326-3325, issn 2072-6651, www.mdpi.com/journal/toxins.

* cited by examiner

SEQUENCE LISTING

```
<160> NUMBER OF SEQ ID NOS: 19

<210> SEQ ID NO 1
<211> LENGTH: 789
<212> TYPE: PRT
<213> ORGANISM: Artificial Sequence
<220> FEATURE:
<223> OTHER INFORMATION: source:  Bacillus thuringiensis

<400> SEQUENCE: 1

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30
```

```
Ile Met Asn Met Ile Phe Lys Thr Asp Thr Gly Gly Asp Leu Thr Leu
         35                  40                  45

Asp Glu Ile Leu Lys Asn Gln Gln Leu Leu Asn Asp Ile Ser Gly Lys
     50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Ile Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445
```

```
Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
770                 775                 780

Asp Val Ser Ile Lys
785

<210> SEQ ID NO 2
<211> LENGTH: 2370
<212> TYPE: DNA
<213> ORGANISM: Artificial Sequence
<220> FEATURE:
<223> OTHER INFORMATION: source: Bacillus thuringiensis

<400> SEQUENCE: 2
atgaacaaga caacaccaa gctgagcacc cgcgccctgc cgagcttcat cgactacttc    60
aacggcatct acggcttcgc caccggcatc aaggacatca tgaacatgat cttcaagacc   120
```

```
gacaccggcg gcgacctgac cctggacgag atcctgaaga accagcagct gctgaacgac      180
atcagcggca agctggacgg cgtgaacggc agcctgaacg acctgatcgc ccagggcaac      240
ctgaacaccg agctgagcaa ggagatcctt aagatcgcca acgagcagaa ccaggtgctg      300
aacgacgtga caacaagct ggacgccatc aacaccatgc tgcgcgtgta cctgccgaag       360
atcaccagca tgctgagcga cgtgattaag cagaactacg ccctgagcct gcagatcgag      420
tacctgagca gcagctgca ggagatcagc gacaagctgg acatcatcaa cgtgaacgtc       480
ctgatcaaca gcaccctgac cgagatcacc ccggcctacc agcgcatcaa gtacgtgaac      540
gagaagttcg aagagctgac cttcgccacc gagaccagca gcaaggtgaa gaaggacggc      600
agcccggccg acatcctgga cgagctgacc gagctgaccg agctggcgaa gagcgtgacc      660
aagaacgacg tggacggctt cgagttctac ctgaacacct ccacgacgt gatggtgggc       720 aacaacctgt tcggccgcag cgccctgaag accgccagcg agctgatcac caaggagaac      780
gtgaagacca cggcagcga ggtgggcaac gtgtacaact tcctgatcgt gctgaccgcc       840
ctgcaggccc aggccttcct gaccctgacc acctgtcgca agctgctggg cctggccgac      900
atcgactaca ccagcatcat gaacgagcac ttgaacaagg agaaggagga gttccgcgtg      960
aacatcctgc cgaccctgag caacaccttc agcaacccga actacgccaa ggtgaagggc      1020
agcgacgagg acgccaagat gatcgtggag gctaagccgg ccacgcgtt gatcggcttc       1080 gagatcagca cgacagcat caccgtgctg aaggtgtacg aggccaagct gaagcagaac       1140
taccaggtgg acaaggacag cttgagcgag gtgatctacg cgacatgga caagctgctg      1200 tgtccggacc agagcgagca aatctactac accaacaaca tcgtgttccc gaacgagtac      1260
gtgatcacca agatcgactt caccaagaag atgaagaccc tgcgctacga ggtgaccgcc      1320
aacttctacg acagcagcac cggcgagatc gacctgaaca agaagaaggt ggagagcagc      1380
gaggccgagt accgcaccct gagcgcgaac gacgacggcg tctacatgcc actgggcgtg      1440
atcagcgaga ccttcctgac cccgatcaac ggctttggcc tgcaggccga cgagaacagc      1500
cgcctgatca ccctgacctg taagagctac ctgcgcgagc tgctgctagc caccgacctg      1560
agcaacaagg agaccaagct gatcgtgcca ccgagcggct tcatcagcaa catcgtggag      1620
aacggcagca tcgaggagga caacctggag ccgtggaagg ccaacaacaa gaacgcctac      1680
gtcgaccaca ccggcggcgt gaacggcacc aaggccctgt acgtgcacaa ggacggcggc      1740
atcagccagt tcatcggcga caagctgaag ccgaagaccg agtacgtgat ccagtacacc      1800
gtgaagggca agccatcgat tcacctgaag gacgagaaca ccggctacat ccactacgag      1860
gacaccaaca caacctgga ggactaccag accatcaaca gcgcttcac caccggcacc        1920 gacctgaagg gcgtgtacct gatcctgaag agccagaacg cgacgaggc ctggggcgac       1980 aacttcatca tcctggagat cagcccgagc gagaagctgc tgagcccgga gctgatcaac      2040
accaacaact ggaccagcac cggcagcacc aacatcagcg caacaccct gacctgtac        2100 cagggcggcc gcggcatcct gaagcagaac ctgcagctgg acagcttcag cacctaccgc      2160
gtgtacttca gcgtgagcgg cgacgccaac gtgcgcatcc gcaactccg cgaggtgctg      2220 ttcgagaaga ggtacatgag cggcgccaag gacgtgagcg agatgttcac caccaagttc      2280
gagaaggaca acttctacat cgagctgagc cagggcaaca acctgtacgg cggcccgatc      2340
gtgcacttct acgacgtgag catcaagtag                                       2370
```

<210> SEQ ID NO 3

```
<211> LENGTH: 789
<212> TYPE: PRT
<213> ORGANISM: Bacillus thuringiensis

<400> SEQUENCE: 3
```

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu

```
                385                 390                 395                 400
            Cys Pro Asp Gln Ser Glu Gln Ile Tyr Tyr Thr Asn Asn Ile Val Phe
                            405                 410                 415

Pro Asn Glu Tyr Val Ile Thr Lys Ile Asp Phe Thr Lys Lys Met Lys
                            420                 425                 430

Thr Leu Arg Tyr Glu Val Thr Ala Asn Phe Tyr Asp Ser Ser Thr Gly
                            435                 440                 445

Glu Ile Asp Leu Asn Lys Lys Lys Val Glu Ser Ser Glu Ala Glu Tyr
                            450                 455                 460

Arg Thr Leu Ser Ala Asn Asp Asp Gly Val Tyr Met Pro Leu Gly Val
            465                 470                 475                 480

Ile Ser Glu Thr Phe Leu Thr Pro Ile Asn Gly Phe Gly Leu Gln Ala
                            485                 490                 495

Asp Glu Asn Ser Arg Leu Ile Thr Leu Thr Cys Lys Ser Tyr Leu Arg
                            500                 505                 510

Glu Leu Leu Leu Ala Thr Asp Leu Ser Asn Lys Glu Thr Lys Leu Ile
                            515                 520                 525

Val Pro Pro Ser Gly Phe Ile Ser Asn Ile Val Glu Asn Gly Ser Ile
                            530                 535                 540

Glu Glu Asp Asn Leu Glu Pro Trp Lys Ala Asn Asn Lys Asn Ala Tyr
            545                 550                 555                 560

Val Asp His Thr Gly Gly Val Asn Gly Thr Lys Ala Leu Tyr Val His
                            565                 570                 575

Lys Asp Gly Gly Ile Ser Gln Phe Ile Gly Asp Lys Leu Lys Pro Lys
                            580                 585                 590

Thr Glu Tyr Val Ile Gln Tyr Thr Val Lys Gly Lys Pro Ser Ile His
                            595                 600                 605

Leu Lys Asp Glu Asn Thr Gly Tyr Ile His Tyr Glu Asp Thr Asn Asn
                            610                 615                 620

Asn Leu Glu Asp Tyr Gln Thr Ile Asn Lys Arg Phe Thr Thr Gly Thr
            625                 630                 635                 640

Asp Leu Lys Gly Val Tyr Leu Ile Leu Lys Ser Gln Asn Gly Asp Glu
                            645                 650                 655

Ala Trp Gly Asp Asn Phe Ile Ile Leu Glu Ile Ser Pro Ser Glu Lys
                            660                 665                 670

Leu Leu Ser Pro Glu Leu Ile Asn Thr Asn Asn Trp Thr Ser Thr Gly
                            675                 680                 685

Ser Thr Asn Ile Ser Gly Asn Thr Leu Thr Leu Tyr Gln Gly Gly Arg
                            690                 695                 700

Gly Ile Leu Lys Gln Asn Leu Gln Leu Asp Ser Phe Ser Thr Tyr Arg
            705                 710                 715                 720

Val Tyr Phe Ser Val Ser Gly Asp Ala Asn Val Arg Ile Arg Asn Ser
                            725                 730                 735

Arg Glu Val Leu Phe Glu Lys Arg Tyr Met Ser Gly Ala Lys Asp Val
                            740                 745                 750

Ser Glu Met Phe Thr Thr Lys Phe Glu Lys Asp Asn Phe Tyr Ile Glu
                            755                 760                 765

Leu Ser Gln Gly Asn Asn Leu Tyr Gly Gly Pro Ile Val His Phe Tyr
                            770                 775                 780

Asp Val Ser Ile Lys
            785

<210> SEQ ID NO 4
```

<211> LENGTH: 2376
<212> TYPE: DNA
<213> ORGANISM: Bacillus thuringiensis

<400> SEQUENCE: 4

| | | | | | |
|---|---|---|---|---|---|
| atgaacatga | acaagaataa | tactaaatta | agcacaagag | ccttaccaag | ttttattgat | 60 |
| tattttaatg | gcatttatgg | atttgccact | ggtatcaaag | acattatgaa | catgattttt | 120 |
| aaaacggata | caggtggtga | tctaacccta | gacgaaattt | taagaatca | gcagttacta | 180 |
| aatgatattt | ctggtaaatt | ggatggggtg | aatggaagct | aaatgatct | tatcgcacag | 240 |
| ggaaacttaa | atacagaatt | atctaaggaa | atattaaaaa | ttgcaaatga | acaaaatcaa | 300 |
| gttttaaatg | atgttaataa | caaactcgat | gcgataaata | cgatgcttcg | gtatatcta | 360 |
| cctaaaatta | cctctatgtt | gagtgatgta | atgaaacaaa | attatgcgct | aagtctgcaa | 420 |
| atagaatact | taagtaaaca | attgcaagag | atttctgata | agttggatat | tattaatgta | 480 |
| aatgtactta | ttaactctac | acttactgaa | attacacctg | cgtatcaaag | gattaaatat | 540 |
| gtgaacgaaa | aatttgagga | attaactttt | gctacagaaa | ctagttcaaa | agtaaaaaag | 600 |
| gatggctctc | ctgcagatat | tcttgatgag | ttaactgagt | taactgaact | agcgaaaagt | 660 |
| gtaacaaaaa | atgatgtgga | tggttttgaa | ttttacctta | atacattcca | cgatgtaatg | 720 |
| gtaggaaata | atttattcgg | gcgttcagct | ttaaaaactg | catcggaatt | aattactaaa | 780 |
| gaaaatgtga | aaacaagtgg | cagtgaggtc | ggaaatgttt | ataacttctt | aattgtatta | 840 |
| acagctctgc | aagcccaagc | ttttcttact | taacaacat | gccgaaaatt | attaggctta | 900 |
| gcagatattg | attatacttc | tattatgaat | gaacatttaa | ataaggaaaa | agaggaattt | 960 |
| agagtaaaca | tcctccctac | actttctaat | acttttttcta | atcctaatta | tgcaaaagtt | 1020 |
| aaaggaagtg | atgaagatgc | aaagatgatt | gtggaagcta | aaccaggaca | tgcattgatt | 1080 |
| gggtttgaaa | ttagtaatga | ttcaattaca | gtattaaaag | tatatgaggc | taagctaaaa | 1140 |
| caaaattatc | aagtcgataa | ggattcctta | tcggaagtta | tttatggtga | tatggataaa | 1200 |
| ttattgtgcc | cagatcaatc | tgaacaaatc | tattatacaa | ataacatagt | atttccaaat | 1260 |
| gaatatgtaa | ttactaaaat | tgatttcact | aaaaaaatga | aaactttaag | atatgaggta | 1320 |
| acagcgaatt | tttatgattc | ttctacagga | gaaattgact | taaataagaa | aaaagtagaa | 1380 |
| tcaagtgaag | cggagtatag | aacgttaagt | gctaatgatg | atggggtgta | tatgccgtta | 1440 |
| ggtgtcatca | gtgaaacatt | tttgactccg | attaatgggt | ttggcctcca | agctgatgaa | 1500 |
| aattcaagat | taattacttt | aacatgtaaa | tcatatttaa | gagaactact | gctagcaaca | 1560 |
| gacttaagca | ataaagaaac | taaattgatc | gtcccgccaa | gtggttttat | tagcaatatt | 1620 |
| gtagagaacg | ggtccataga | agaggacaat | ttagagccgt | ggaaagcaaa | taataagaat | 1680 |
| gcgtatgtag | atcatacagg | cggagtgaat | ggaactaaag | ctttatatgt | tcataaggac | 1740 |
| ggaggaattt | cacaatttat | tggagataag | ttaaaaccga | aactgagta | tgtaatccaa | 1800 |
| tatactgtta | aaggaaaacc | ttctattcat | ttaaaagatg | aaaatactgg | atatattcat | 1860 |
| tatgaagata | caaataataa | tttagaagat | tatcaaacta | ttaataaacg | ttttactaca | 1920 |
| ggaactgatt | taagggagt | gtatttaatt | ttaaaaagtc | aaaatggaga | tgaagcttgg | 1980 |
| ggagataact | ttattatttt | ggaaattagt | ccttctgaaa | agttattaag | tccagaatta | 2040 |
| attaatacaa | ataattggac | gagtacggga | tcaactaata | ttagcggtaa | tacactcact | 2100 |
| ctttatcagg | gaggacgagg | gattctaaaa | caaaaccttc | aattagatag | tttttcaact | 2160 |
| tatagagtgt | attttctgt | gtccggagat | gctaatgtaa | ggattagaaa | ttctagggaa | 2220 |

```
gtgttatttg aaaaaagata tatgagcggt gctaaagatg tttctgaaat gttcactaca   2280
aaatttgaga aagataactt ttatatagag ctttctcaag ggaataattt atatggtggt   2340
cctattgtac atttttacga tgtctctatt aagtaa                             2376

<210> SEQ ID NO 5
<211> LENGTH: 2370
<212> TYPE: DNA
<213> ORGANISM: Artificial Sequence
<220> FEATURE:
<223> OTHER INFORMATION: Source:  Bacillus thuringiensis

<400> SEQUENCE: 5
atgaacaaga acaacaccaa gctgagcacc cgcgccctgc cgagcttcat cgactacttc     60
aacggcatct acggcttcgc caccggcatc aaggacatca tgaacatgat cttcaagacc    120
gacaccggcg gcgacctgac cctggacgag atcctgaaga accagcagct gctgaacgac    180
atcagcggca agctggacgg cgtgaacggc agcctgaacg acctgatcgc ccagggcaac    240
ctgaacaccg agctgagcaa ggagatcctt aagatcgcca acgagcagaa ccaggtgctg    300
aacgacgtga acaacaagct ggacgccatc aacaccatgc tgcgcgtgta cctgccgaag    360
atcaccagca tgctgagcga cgtgatgaag cagaactacg ccctgagcct gcagatcgag    420
tacctgagca agcagctgca ggagatcagc gacaagctgg acatcatcaa cgtgaacgtc    480
ctgatcaaca gcaccctgac cgagatcacc ccggcctacc agcgcatcaa gtacgtgaac    540
gagaagttcg aagagctgac cttcgccacc gagaccagca gcaaggtgaa gaaggacggc    600
agcccggccg acatcctgga cgagctgacc gagctgaccg agctggcgaa gagcgtgacc    660
aagaacgacg tggacggctt cgagttctac ctgaacacct tccacgacgt gatggtgggc    720
aacaacctgt tcggccgcag cgccctgaag accgccagcg agctgatcac caaggagaac    780
gtgaagacca gcggcagcga ggtgggcaac gtgtacaact tcctgatcgt gctgaccgcc    840
ctgcaggccc aggccttcct gaccctgacc acctgtcgca agctgctggg cctggccgac    900
atcgactaca ccagcatcat gaacgagcac ttgaacaagg agaaggagga gttccgcgtg    960
aacatcctgc cgaccctgag caacaccttc agcaacccga actacgccaa ggtgaagggc   1020
agcgacgagg acgccaagat gatcgtggag gctaagccgg gccacgcgtt gatcggcttc   1080
gagatcagca acgacagcat caccgtgctg aaggtgtacg aggccaagct gaagcagaac   1140
taccaggtgg acaaggacag cttgagcgag gtgatctacg gcgacatgga caagctgctg   1200
tgtccggacc agagcgagca aatctactac accaacaaca tcgtgttccc gaacgagtac   1260
gtgatcacca agatcgactt caccaagaag atgaagaccc tgcgctacga ggtgaccgcc   1320
aacttctacg acagcagcac cggcgagatc gacctgaaca agaagaaggt ggagagcagc   1380
gaggccgagt accgcaccct gagcgcgaac gacgacggcg tctacatgcc actgggcgtg   1440
atcagcgaga ccttcctgac cccgatcaac ggctttggcc tgcaggccga cgagaacagc   1500
cgcctgatca ccctgacctg taagagctac ctgcgcgagc tgctgctagc caccgacctg   1560
agcaacaagg agaccaagct gatcgtgcca ccgagcggct tcatcagcaa catcgtggag   1620
aacggcagca tcgaggagga caacctggag ccgtggaagg ccaacaacaa gaacgcctac   1680
gtggaccaca ccggcggcgt gaacggcacc aaggccctgt acgtgcacaa ggacggcggc   1740
atcagccagt tcatcggcga caagctgaag ccgaagaccg agtacgtgat ccagtacacc   1800
gtgaagggca agccatcgat tcacctgaag gacgagaaca ccggctacat ccactacgag   1860
```

```
gacaccaaca caacctggaa ggactaccag accatcaaca agcgcttcac caccggcacc      1920
gacctgaagg gcgtgtacct gatcctgaag agccagaacg gcgacgaggc ctggggcgac      1980
aacttcatca tcctggagat cagcccgagc gagaagctgc tgagcccgga gctgatcaac      2040
accaacaact ggaccagcac cggcagcacc aacatcagcg gcaacaccct gaccctgtac      2100
cagggcggcc gcggcatcct gaagcagaac ctgcagctgg acagcttcag cacctaccgc      2160
gtgtacttca gcgtgagcgg cgacgccaac gtgcgcatcc gcaactcccg cgaggtgctg      2220
ttcgagaaga ggtacatgag cggcgccaag gacgtgagcg agatgttcac caccaagttc      2280
gagaaggaca acttctacat cgagctgagc cagggcaaca acctgtacgg cggcccgatc      2340
gtgcacttct acgacgtgag catcaagtag                                       2370
```

<210> SEQ ID NO 6
<211> LENGTH: 789
<212> TYPE: PRT
<213> ORGANISM: Bacillus thuringiensis

<400> SEQUENCE: 6

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Arg Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285
```

```
Leu Thr Pro Cys Arg Lys Leu Leu Gly Leu Ala Asp Ile Asp Tyr Thr
290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
                340                 345                 350

Pro Gly His Ala Leu Ile Gly Phe Glu Ile Ser Asn Asp Ser Ile Thr
                355                 360                 365

Val Leu Lys Val Tyr Glu Ala Lys Leu Lys Gln Asn Tyr Gln Val Asp
370                 375                 380

Lys Asp Ser Leu Ser Glu Val Ile Tyr Gly Asp Met Asp Lys Leu Leu
385                 390                 395                 400

Cys Pro Asp Gln Ser Gly Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
                435                 440                 445

Glu Ile Asp Leu Asn Lys Lys Lys Val Glu Ser Ser Glu Ala Glu Tyr
450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
                515                 520                 525

Val Pro Pro Ser Gly Phe Ile Ser Asn Ile Val Glu Asn Gly Ser Ile
530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
                595                 600                 605

Leu Lys Asp Glu Asn Thr Gly Tyr Ile His Tyr Glu Asp Thr Asn Asn
610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Asn Trp Thr Ser Thr Gly
                675                 680                 685

Ser Thr Asn Ile Ser Gly Asn Thr Leu Thr Leu Tyr Gln Gly Gly Arg
690                 695                 700
```

```
Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
    770                 775                 780

Asp Val Ser Ile Lys
785

<210> SEQ ID NO 7
<211> LENGTH: 2376
<212> TYPE: DNA
<213> ORGANISM: Bacillus thuringiensis

<400> SEQUENCE: 7
```

| | | | | | |
|---|---|---|---|---|---|
| atgaacatga | acaagaataa | tactaaatta | agcacaagag | ccttaccaag | ttttattgat | 60 |
| tatttcaatg | gcatttatgg | atttgccact | ggtatcaaag | acattatgaa | catgattttt | 120 |
| aaaacggata | caggtggtga | tctaacccta | gacgaaattt | taagaatca | gcagctacta | 180 |
| aatgatattt | ctggtaaatt | ggatggggtg | aatggaagct | taaatgatct | tatcgcacag | 240 |
| ggaaacttaa | atacagaatt | atctaaggaa | atattaaaaa | ttgcaaatga | acaaaatcaa | 300 |
| gttttaaatg | atgttaataa | caaactcgat | gcgataaata | cgatgcttcg | ggtatatcta | 360 |
| cctaaaatta | cctctatgtt | gagtgatgta | atgaaacaaa | attatgcgct | aagtctgcaa | 420 |
| atagaatact | taagtaaaca | attgcaagag | atttctgata | agttggatat | tattaatgta | 480 |
| aatgtactta | ttaactctac | acttactgaa | attcacctg | cgtatcaaag | gattaaatat | 540 |
| gtgaacgaaa | aatttgagga | attaactttt | gctacagaaa | ctagttcaaa | agtaaaaaag | 600 |
| gatggctctc | ctgcagatat | tcgtgatgag | ttaactgagt | taactgaact | agcgaaaagt | 660 |
| gtaacaaaaa | atgatgtgga | tggttttgaa | ttttacctta | tacattcca | cgatgtaatg | 720 |
| gtaggaaata | atttattcgg | gcgttcagct | ttaaaaactg | catcggaatt | aattactaaa | 780 |
| gaaaatgtga | aaacaagtgg | cagtgaggtc | ggaaatgttt | ataacttcct | aattgtatta | 840 |
| acagctctgc | aagcaaaagc | ttttcttact | ttaacaccat | gccgaaaatt | attaggctta | 900 |
| gcagatattg | attatacttc | tattatgaat | gaacatttaa | ataaggaaaa | agaggaattt | 960 |
| agagtaaaca | tcctccctac | actttctaat | acttttccta | atcctaatta | tgcaaaagtt | 1020 |
| aaaggaagtg | atgaagatgc | aaagatgatt | gtggaagcta | aaccaggaca | tgcattgatt | 1080 |
| gggtttgaaa | ttagtaatga | ttcaattaca | gtattaaaag | tatatgaggc | taagctaaaa | 1140 |
| caaaattatc | aagtcgataa | ggattcctta | tcggaagtta | tttatggcga | tatggataaa | 1200 |
| ttattgtgcc | cagatcaatc | tggacaaatc | tattatacaa | ataacatagt | atttccaaat | 1260 |
| gaatatgtaa | ttactaaaat | tgatttcact | aaaaaaatga | aactttaag | atatgaggta | 1320 |
| acagcgaatt | tttatgattc | ttctacagga | gaaattgact | aaataagaa | aaagtagaa | 1380 |
| tcaagtgaag | cggagtatag | aacgttaagt | gctaatgatg | atggggtgta | tatgccgtta | 1440 |
| ggtgtcatca | gtgaaacatt | tttgactccg | attaatgggt | ttggcctcca | agctgatgaa | 1500 |
| aattcaagat | taattacttt | aacatgtaaa | tcatatttaa | gagaactact | gctagcaaca | 1560 |
| gacttaagca | ataaagaaac | taaattgatc | gtcccgccaa | gtggttttat | tagcaatatt | 1620 |

```
gtagagaacg ggtccataga agaggacaat ttagagccgt ggaaagcaaa taataagaat   1680
gcgtatgtag atcatacagg cggagtgaat ggaactaaag ctttatatgt tcataaggac   1740
ggaggaattt cacaatttat tggagataag ttaaaaccga aaactgagta tgtaatccaa   1800
tatactgtta aaggaaaacc ttctattcat ttaaaagatg aaaatactgg atatattcat   1860
tatgaagata caaataataa tttagaagat tatcaaacta ttaataaacg ttttactaca   1920
ggaactgatt taaagggagt gtatttaatt ttaaaaagtc aaaatggaga tgaagcttgg   1980
ggagataact ttattatttt ggaaattagt ccttctgaaa agttattaag tccagaatta   2040
attaatacaa ataattggac gagtacggga tcaactaata ttagcggtaa tacactcact   2100
ctttatcagg gaggacgagg gattctaaaa caaaaccttc aattagatag ttttcaact     2160 tatagagtgt atttctctgt gtccggagat gctaatgtaa ggattagaaa ttctagggaa   2220
gtgttatttg aaaaaagata tatgagcggt gctaaagatg tttctgaaat gttcactaca   2280
aaatttgaga agataacttt ctatatagag ctttctcaag gaataaattt atatggtggt   2340
cctattgtac attttacga tgtctctatt aagtaa                              2376
```

<210> SEQ ID NO 8
<211> LENGTH: 748
<212> TYPE: PRT
<213> ORGANISM: Bacillus thuringiensis

<400> SEQUENCE: 8

```
Met Asn Met Asn Lys Asn Asn Ala Lys Leu Ser Thr Arg Ala Leu Pro
1               5                   10                  15

Ser Phe Ile Asp Tyr Phe Asn Gly Ile Tyr Gly Phe Ala Thr Gly Ile
            20                  25                  30

Lys Asp Ile Met Asn Met Ile Phe Lys Thr Asp Thr Gly Gly Asp Leu
        35                  40                  45

Ala Leu Asp Glu Ile Leu Glu Asn Gln Gln Leu Leu Asn Asp Ile Ser
    50                  55                  60

Gly Lys Leu Asp Gly Val Asn Gly Ser Leu Asn Asp Leu Ile Ala Gln
65                  70                  75                  80

Gly Asn Leu Asn Thr Glu Leu Ser Lys Glu Ile Leu Lys Ile Ala Asn
                85                  90                  95

Glu Gln Asn Gln Val Leu Asn Asp Val Asn Asn Lys Leu Asp Ala Ile
            100                 105                 110

Asn Thr Met Leu Arg Val Tyr Leu Pro Lys Ile Thr Ser Met Leu Ser
        115                 120                 125

Asp Val Met Lys Gln Asn Tyr Ala Leu Ser Leu Gln Ile Glu Tyr Leu
    130                 135                 140

Ser Lys Gln Leu Gln Glu Ile Ser Asp Lys Leu Asp Ile Ile Asn Val
145                 150                 155                 160

Asn Val Leu Ile Asn Ser Thr Leu Thr Glu Ile Thr Pro Ala Tyr Gln
                165                 170                 175

Arg Ile Lys Tyr Val Asn Glu Lys Phe Glu Glu Leu Thr Phe Ala Thr
            180                 185                 190

Glu Thr Ser Ser Lys Val Lys Lys Asp Gly Ser Pro Ala Asp Ile Arg
        195                 200                 205

Asp Glu Leu Ser Glu Leu Thr Glu Leu Ala Lys Ser Val Thr Gln Asn
    210                 215                 220

Asp Val Asp Gly Phe Glu Phe Tyr Leu Asn Thr Phe His Asp Val Met
225                 230                 235                 240
```

```
Val Gly Asn Asn Leu Phe Gly Arg Ser Ala Leu Lys Thr Ala Ser Glu
                245                 250                 255

Leu Ile Thr Lys Glu Asn Val Lys Thr Ser Gly Ser Glu Val Gly Asn
            260                 265                 270

Val Tyr Asn Phe Leu Ile Val Leu Thr Ala Leu Gln Ala Gln Ala Phe
        275                 280                 285

Leu Thr Leu Thr Pro Cys Arg Lys Leu Leu Gly Leu Ala Asp Ile Asp
    290                 295                 300

Tyr Thr Ser Ile Met Asn Glu His Leu Asn Lys Glu Lys Glu Glu Phe
305                 310                 315                 320

Arg Val Asn Ile Leu Pro Thr Leu Ser Asn Thr Phe Ser Asn Pro Asn
                325                 330                 335

Tyr Ala Lys Val Lys Gly Ser Asp Glu Asp Ala Lys Met Ile Val Glu
            340                 345                 350

Ala Lys Pro Gly His Ala Leu Ile Gly Phe Glu Ile Ser Asn Asp Ser
        355                 360                 365

Ile Thr Val Leu Lys Val Tyr Glu Ala Lys Leu Lys Gln Asn Tyr Gln
    370                 375                 380

Val Asp Lys Asp Ser Leu Ser Glu Val Ile Tyr Gly Asp Met Asp Lys
385                 390                 395                 400

Leu Leu Cys Pro Asp Gln Ser Gly Gln Ile Tyr Tyr Thr Asn Asn Ile
                405                 410                 415

Val Phe Pro Asn Glu Tyr Val Ile Thr Lys Ile Asp Phe Thr Lys Lys
            420                 425                 430

Met Lys Thr Leu Arg Tyr Glu Val Thr Ala Asn Phe Tyr Asp Ser Ser
        435                 440                 445

Thr Gly Glu Ile Asp Leu Asn Lys Lys Val Glu Ser Ser Glu Ala
    450                 455                 460

Glu Tyr Arg Thr Leu Ser Ala Asn Asp Asp Gly Val Tyr Met Pro Leu
465                 470                 475                 480

Gly Val Ile Ser Glu Thr Phe Leu Thr Pro Ile Asn Gly Phe Gly Leu
                485                 490                 495

Gln Ala Asp Glu Asn Ser Arg Leu Ile Thr Leu Thr Cys Lys Ser Tyr
            500                 505                 510

Leu Arg Glu Leu Leu Leu Ala Thr Asp Leu Ser Asn Lys Glu Thr Lys
        515                 520                 525

Leu Ile Val Pro Pro Ser Gly Phe Ile Ser Asn Ile Val Glu Asn Gly
    530                 535                 540

Ser Ile Glu Glu Asp Asn Leu Glu Pro Trp Lys Ala Asn Asn Lys Asn
545                 550                 555                 560

Ala Tyr Val Asp His Thr Gly Gly Val Asn Gly Thr Lys Ala Leu Tyr
                565                 570                 575

Val His Lys Asp Gly Gly Ile Ser Gln Phe Ile Gly Asp Lys Leu Lys
            580                 585                 590

Pro Lys Thr Glu Tyr Val Ile Gln Tyr Thr Val Lys Gly Lys Pro Ser
        595                 600                 605

Ile His Leu Lys Asp Glu Asn Thr Gly Tyr Ile His Tyr Glu Asp Thr
    610                 615                 620

Asn Asn Asn Leu Glu Asp Tyr Gln Thr Ile Asn Lys Arg Phe Thr Thr
625                 630                 635                 640

Gly Thr Asp Leu Lys Gly Val Tyr Leu Ile Leu Lys Ser Gln Asn Gly
                645                 650                 655
```

-continued

```
Asp Glu Ala Trp Gly Asp Asn Phe Ile Ile Leu Glu Ile Ser Pro Ser
            660                 665                 670

Glu Lys Leu Leu Ser Pro Glu Leu Ile Asn Thr Asn Asn Trp Thr Ser
        675                 680                 685

Thr Gly Ser Thr Asn Ile Ser Gly Asn Thr Leu Thr Leu Tyr Gln Gly
    690                 695                 700

Gly Arg Gly Ile Leu Lys Gln Asn Leu Gln Leu Asp Ser Phe Ser Thr
705                 710                 715                 720

Tyr Arg Val Tyr Phe Ser Val Ser Gly Asp Ala Asn Val Arg Ile Arg
                725                 730                 735

Asn Ser Arg Glu Val Leu Phe Glu Lys Lys Asp Ile
            740                 745

<210> SEQ ID NO 9
<211> LENGTH: 2247
<212> TYPE: DNA
<213> ORGANISM: Bacillus thuringiensis

<400> SEQUENCE: 9
atgaacatga acaagaataa tgctaaatta agcacaagag ccttaccaag ttttattgat      60
tatttcaatg gcatttatgg atttgccact ggtatcaaag acattatgaa catgattttt     120
aaaacggata caggtggtga tctagcccta gacgaaattt tagagaatca gcagctacta     180
aatgatattt ctggtaaatt ggatggggtg aatggaagct taaatgatct tatcgcacag     240
ggaaacttaa atacagaatt atctaaggaa atattaaaaa ttgcaaatga acaaaatcaa     300
gttttaaatg atgttaataa caaactcgat gcgataaata cgatgcttcg ggtatatcta     360
cctaaaatta cctctatgtt gagtgatgta atgaaacaaa attatgcgct aagtctgcaa     420
atagaatact taagtaaaca attgcaagag atttctgata agttggatat tattaatgta     480
aatgtactta ttaactctac acttactgaa attacacctg cgtatcaaag gattaaatat     540
gtgaacgaaa aatttgagga attaactttt gctacagaaa ctagttcaaa agtaaaaaag     600
gatggctctc ctgcagatat tcgtgatgag ttaagtgagt taactgaact agcgaaaagt     660
gtaacacaaa atgatgtgga tggttttgaa ttttacctta atacattcca cgatgtaatg     720
gtaggaaata atttattcgg gcgttcagct ttaaaaactg catcggaatt aattactaaa     780
gaaaatgtga aaacaagtgg cagtgaggtc ggaaatgttt ataacttcct aattgtatta     840
acagctctgc aagcacaagc ttttcttact ttaacaccat gccgaaaatt attaggctta     900
gcagatattg attatacttc tattatgaat gaacatttaa ataaggaaaa agaggaattt     960
agagtaaaca tcctccctac actttctaat actttttcta atcctaatta tgcaaaagtt    1020
aaaggaagtg atgaagatgc aaagatgatt gtggaagcta aaccaggaca tgcattgatt    1080
gggtttgaaa ttagtaatga ttcaattaca gtattaaaag tatatgaggc taagctaaaa    1140
caaaattatc aagtcgataa ggattcctta tcggaagtta tttatggcga tatggataaa    1200
ttattgtgcc cagatcaatc tggacaaatc tattatacaa ataacatagt atttccaaat    1260
gaatatgtaa ttactaaaat tgatttcact aaaaaaatga aaactttaag atatgaggta    1320
acagcgaatt tttatgattc ttctacagga gaaattgact taaataagaa aaaagtagaa    1380
tcaagtgaag cggagtatag aacgttaagt gctaatgatg atggggtgta tatgccgtta    1440
ggtgtcatca gtgaaacatt tttgactccg attaatgggt ttggcctcca agctgatgaa    1500
aattcaagat taattacttt aacatgtaaa tcatatttaa gagaactact gctagcaaca    1560
gacttaagca ataaagaaac taaattgatc gtcccgccaa gtggttttat tagcaatatt    1620
```

-continued

```
gtagagaacg ggtccataga agaggacaat ttagagccgt ggaaagcaaa taataagaat      1680
gcgtatgtag atcatacagg cggagtgaat ggaactaaag ctttatatgt tcataaggac      1740
ggaggaattt cacaatttat tggagataag ttaaaaccga aaactgagta tgtaatccaa      1800
tatactgtta aaggaaaacc ttctattcat ttaaaagatg aaaatactgg atatattcat      1860
tatgaagata caaataataa tttagaagat tatcaaacta ttaataaacg ttttactaca      1920
ggaactgatt taaagggagt gtatttaatt ttaaaaagtc aaaatggaga tgaagcttgg      1980
ggagataact ttattatttt ggaaattagt ccttctgaaa agttattaag tccagaatta      2040
attaatacaa ataattggac gagtacggga tcaactaata ttagcggtaa tacactcact      2100
ctttatcagg gaggacgagg gattctaaaa caaaaccttc aattagatag ttttttcaact      2160 tatagagtgt atttctctgt gtccggagat gctaatgtaa ggattagaaa ttctagggaa      2220
gtgttatttg aaaaaaagga tatatga                                          2247
```

<210> SEQ ID NO 10
<211> LENGTH: 788
<212> TYPE: PRT
<213> ORGANISM: Bacillus thuringiensis

<400> SEQUENCE: 10

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255
```

-continued

```
Ala Lys Glu Asn Val Lys Thr Ser Gly Ser Glu Val Gly Asn Val Tyr
            260                 265                 270
Asn Phe Leu Ile Val Leu Thr Ala Leu Gln Ala Lys Ala Phe Leu Thr
        275                 280                 285
Leu Thr Thr Cys Arg Lys Leu Leu Gly Leu Ala Gly Ile Asp Tyr Thr
290                 295                 300
Ser Ile Met Asn Glu His Leu Asn Lys Glu Lys Glu Phe Arg Val
305                 310                 315                 320
Asn Ile Leu Pro Thr Leu Ser Asn Thr Phe Ser Asn Pro Asn Tyr Ala
                325                 330                 335
Lys Val Lys Gly Ser Asp Glu Asp Ala Lys Met Ile Val Glu Ala Lys
            340                 345                 350
Pro Gly His Ala Leu Val Gly Phe Glu Met Ser Asn Asp Ser Ile Thr
        355                 360                 365
Val Leu Lys Val Tyr Glu Ala Lys Leu Lys Gln Asn Tyr Gln Val Asp
    370                 375                 380
Lys Asp Ser Leu Ser Glu Val Ile Tyr Gly Asp Thr Asp Lys Leu Phe
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
            420                 425                 430
Thr Leu Arg Tyr Glu Val Thr Ala Asn Phe Tyr Asp Ser Ser Thr Gly
        435                 440                 445
Glu Ile Asp Leu Asn Lys Lys Val Glu Ser Ser Glu Ala Glu Tyr
    450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
        515                 520                 525
Val Pro Pro Ser Gly Phe Ile Ser Asn Ile Val Glu Asn Gly Ser Ile
    530                 535                 540
Glu Glu Asp Asn Leu Glu Pro Trp Lys Ala Asn Asn Lys Asn Ala Tyr
545                 550                 555                 560
Val Asp His Thr Gly Gly Val Asn Gly Thr Lys Ala Leu Tyr Val His
                565                 570                 575
Lys Asp Gly Gly Phe Ser Gln Phe Ile Gly Asp Lys Leu Lys Pro Lys
            580                 585                 590
Thr Glu Tyr Val Ile Gln Tyr Thr Val Lys Gly Lys Pro Ser Ile His
        595                 600                 605
Leu Lys Asp Glu Asn Thr Gly Tyr Ile His Tyr Glu Asp Thr Asn Asn
    610                 615                 620
Asn Leu Lys Asp Tyr Gln Thr Ile Thr Lys Arg Phe Thr Thr Gly Thr
625                 630                 635                 640
Asp Leu Lys Gly Val Tyr Leu Ile Leu Lys Ser Gln Asn Gly Asp Glu
                645                 650                 655
Ala Trp Gly Asp Lys Phe Thr Ile Leu Glu Ile Lys Pro Ala Glu Asp
            660                 665                 670
Leu Leu Ser Pro Glu Leu Ile Asn Pro Asn Ser Trp Ile Thr Thr Pro
```

```
                    675                 680                 685
Gly Ala Ser Ile Ser Gly Asn Lys Leu Phe Ile Asn Leu Gly Thr Asn
                690                 695                 700

Gly Thr Phe Arg Gln Ser Leu Ser Leu Asn Ser Tyr Ser Thr Tyr Ser
705                 710                 715                 720

Ile Ser Phe Thr Ala Ser Gly Pro Phe Asn Val Thr Val Arg Asn Ser
                725                 730                 735

Arg Gly Val Leu Phe Glu Arg Ser Asn Leu Met Ser Ser Thr Ser His
                740                 745                 750

Ile Ser Gly Thr Phe Lys Thr Glu Ser Asn Asn Thr Gly Leu Tyr Val
                755                 760                 765

Glu Leu Ser Arg Arg Ser Gly Gly Gly His Ile Ser Phe Glu Asn
                770                 775                 780

Val Ser Ile Lys
785

<210> SEQ ID NO 11
<211> LENGTH: 2372
<212> TYPE: DNA
<213> ORGANISM: Bacillus thuringiensis

<400> SEQUENCE: 11
atgaacaaga ataatactaa attaagcaca agagccctac cgagtttat tgattatttt      60 aatggcattt atggatttgc cactggtatc aaagacatta tgaatatgat ttttaaaacg    120
gatacaggtg gtaatctaac cttagacgaa atcctaaaga atcagcagtt actaaatgag    180
atttctggta aattggatgg ggtaaatggg agcttaaatg atcttatcgc acagggaaac    240
ttaaatacag aattatctaa ggaaatctta aaaatcgcaa atgaacagaa tcaagtctta    300
aatgatgtta ataacaaact cgatgcgata aatacgatgc ttcatatata tctacctaaa    360
attacatcta tgttaagtga tgtaatgaag caaaattatg cgctaagtct gcaaatagaa    420
tacttaagta agcaattgca agaaatttct gataaattag atattattaa cgtaaatgtt    480
cttattaact ctacacttac tgaaattaca cctgcatatc aacggattaa atatgtgaat    540
gaaaaatttg aagaattaac ttttgctaca gaaaccactt taaaagtaaa aaaggatagc    600
tcgcctgctg atattcttga tgagttaact gaattaactg aactagcgaa aagtgttaca    660
aaaaatgacg ttgatggttt tgaatttac cttaatacat tccacgatgt aatggtagga    720
ataaatttat tcgggcgttc agcttttaaaa actgcttcag aattaattgc taagaaaat    780 gtgaaaacaa gtggcagtga agtaggaaat gtttataatt tcttaattgt attaacagct    840
ctacaagcaa aagctttct tactttaaca acatgccgaa aattattagg cttagcaggt    900
attgattata cttctattat gaatgaacat ttaataagg aaaagagga atttagagta     960 aacatccttc ctacactttc taatactttt tctaatccta attatgcaaa agttaaagga   1020
agtgatgaag atgcaaagat gattgtggaa gctaaaccag acatgcatt ggttgggttt   1080 gaaatgagca atgattcaat cacagtatta aaagtatatg aggctaagct aaaacaaaat   1140
tatcaagttg ataaggattc cctatcggag gttatttatg gtgataccgga taaattattt   1200 tgtccagatc aatctgaaca aatatattat acaaataaca tagtattccc aaatgaatat   1260
gtaattacta aaattgattt cactaaaaaa atgaaaactt taagatatga ggtaacagcg   1320 aattttatg attcttctac aggagaaatt gacttaaata agaaaaagt agaatcaagt   1380 gaagcggagt atagaacgtt aagtgctaat gatgatggag tgtatatgcc attaggtgtc   1440
```

```
atcagtgaaa cattttttgac tccgataaat gggtttggcc tccaagctga tgaaaattca   1500
agattaatta ctttaacatg taaatcatat ttaagagaac tactgctagc aacagactta   1560
agcaataaag aaactaaatt gatcgtccca ccaagtggtt ttattagcaa tattgtagag   1620
aacgggtcca tagaagagga caatttagag ccgtggaaag caataataa gaatgcgtat    1680 gtagatcata caggcggagt gaatggaact aaagctttat atgttcataa ggacggagga   1740
ttttcacaat ttattggaga taagttaaaa ccgaaaactg agtatgtaat ccaatatact   1800
gttaaaggaa aaccttctat tcatttaaaa gatgaaaata ctggatatat tcattatgaa   1860
gatacaaata taatttaaa agattatcaa actattacta aacgttttac tacaggaact    1920
gatttaaagg gagtgtattt aattttaaaa agtcaaaatg gagatgaagc ttggggagat   1980
aaatttacaa ttttagaaat taagcctgcg gaggatttat taagcccaga attaattaat   2040
ccgaattctt ggattacgac tccaggggct agcatttcag gaaataaact tttcattaac   2100
ttggggacaa atgggaccttt tagacaaagt ctttcattaa acagttattc aacttatagt   2160
ataagcttta ctgcatcagg accatttaat gtgacggtaa gaaattctag gggagtatta   2220
tttgaacgaa gcaaccttat gtcttcaact agtcatattt ctgggacatt caaaactgaa   2280
tccaataata ccggattata tgtagaactt tcccgtcgct ctggtggtgg tggtcatata   2340
tcatttgaaa acgtttctat taaataaaaa gg                                 2372
```

<210> SEQ ID NO 12
<211> LENGTH: 788
<212> TYPE: PRT
<213> ORGANISM: Bacillus thuringiensis

<400> SEQUENCE: 12

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

```
Leu Thr Glu Leu Thr Glu Leu Ala Lys Ser Val Thr Lys Asn Asp Val
210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Gly Ile Asp Tyr Thr
290                 295                 300

Ser Ile Met Asn Glu His Leu Asn Lys Glu Lys Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp
370                 375                 380

Lys Asp Ser Leu Ser Glu Val Ile Tyr Gly Asp Thr Lys Leu Phe
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Val Glu Ser Glu Ala Glu Tyr
450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Phe Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
610                 615                 620

Asn Leu Lys Asp Tyr Gln Thr Ile Thr Lys Arg Phe Thr Thr Gly Thr
```

```
                625                 630                 635                 640
Asp Leu Lys Gly Val Tyr Leu Ile Leu Lys Ser Gln Asn Gly Asp Glu
                    645                 650                 655
Ala Trp Gly Asp Lys Phe Thr Ile Leu Glu Ile Lys Pro Ala Glu Asp
                    660                 665                 670
Leu Leu Ser Pro Glu Leu Ile Asn Pro Asn Ser Trp Ile Thr Thr Pro
                675                 680                 685
Gly Ala Ser Ile Ser Gly Asn Lys Leu Phe Ile Asn Leu Gly Thr Asn
            690                 695                 700
Gly Thr Phe Arg Gln Ser Leu Ser Leu Asn Ser Tyr Ser Thr Tyr Ser
705                 710                 715                 720
Ile Ser Phe Thr Ala Ser Gly Pro Phe Asn Val Thr Val Arg Asn Ser
                    725                 730                 735
Arg Glu Val Leu Phe Glu Arg Ser Asn Leu Met Ser Ser Thr Ser His
                740                 745                 750
Ile Ser Gly Thr Phe Lys Thr Glu Ser Asn Asn Thr Gly Leu Tyr Val
                755                 760                 765
Glu Leu Ser Arg Arg Ser Gly Gly Gly Gly His Ile Ser Phe Glu Asn
                770                 775                 780
Val Ser Ile Lys
785

<210> SEQ ID NO 13
<211> LENGTH: 2372
<212> TYPE: DNA
<213> ORGANISM: Bacillus thuringiensis

<400> SEQUENCE: 13
atgaacaaga ataatactaa attaagcaca agagccctac cgagtttttat tgattatttt      60
aatggcattt atggatttgc cactggtatc aaagacatta tgaatatgat ttttaaaacg     120
gatacaggtg gtaatctaac cttagacgaa atcctaaaga atcagcagtt actaaatgag     180
atttctggta aattggatgg ggtaaatggg agcttaaatg atcttatcgc acagggaaac     240
ttaaatacag aattatctaa ggaaatctta aaaatcgcaa atgaacagaa tcaagtctta     300
aatgatgtta ataacaaact cgatgcgata aatacgatgc ttcatatata tctacctaaa     360
attacatcta tgttaagtga tgtaatgaag caaaattatg cgctaagtct gcaaatagaa     420
tacttaagta agcaattgca agaaatttct gataaattag atattattaa cgtaaatgtt     480
cttattaact ctacacttac tgaaattaca cctgcatatc aacggattaa atatgtgaat     540
gaaaaatttg aagaattaac ttttgctaca gaaaccactt taaaagtaaa aaaggatagc     600
tcgcctgctg atattcttga tgagttaact gaattaactg aactagcgaa aagtgttaca     660
aaaaatgacg ttgatggttt tgaattttac cttaatacat tccacgatgt aatggtagga     720
aataatttat tcgggcgttc agcttttaaaa actgcttcag aattaattgc taaagaaaat     780
gtgaaaacaa gtggcagtga agtaggaaat gtttataatt tcttaattgt attaacagct     840
ctacaagcaa aagcttttct tactttaaca acatgccgaa aattattagg cttagcaggt     900
attgattata cttctattat gaatgaacat ttaaataagg aaaagaggaa atttagagta     960
aacatccttc ctacactttc taatactttt tctaatccta attatgcaaa agttaaagga    1020
agtgatgaag atgcaaagat gattgtggaa gctaaaccag acatgcattt ggtttgggttt    1080
gaaatgagca atgattcaat cacagtatta aagtatatg aggctaagct aaaacaaaat     1140
tatcaagttg ataaggattc cctatcggag gttatttatg gtgatacgga taattatttt    1200
```

```
tgtccagatc aatctgaaca aatatattat acaaataaca tagtattccc aaatgaatat    1260
gtaattacta aaattgattt cactaaaaaa atgaaaactt taagatatga ggtaacagcg    1320 aattttatg attcttctac aggagaaatt gacttaaata agaaaaagt agaatcaagt      1380 gaagcggagt atagaacgtt aagtgctaat gatgatggag tgtatatgcc attaggtgtc    1440
atcagtgaaa cattttgac tccgataaat gggtttggcc tccaagctga tgaaaattca    1500
agattaatta ctttaacatg taaatcatat ttaagagaac tactgctagc aacagactta    1560
agcaataaag aaactaaatt gatcgtccca ccaagtggtt ttattagcaa tattgtagag    1620
aacgggtcca tagaagagga caatttagag ccgtggaaag caaataataa gaatgcgtat    1680
gtagatcata caggcggagt gaatggaact aaagctttat atgttcataa ggacggagga    1740
ttttcacaat ttattggaga taagttaaaa ccgaaaactg agtatgtaat ccaatatact    1800
gttaaaggaa aaccttctat tcatttaaaa gatgaaaata ctggatatat tcattatgaa    1860
gatacaaata ataatttaaa agattatcaa actattacta aacgttttac tacaggaact    1920
gatttaaagg gagtgtattt aattttaaaa agtcaaaatg gagatgaagc ttggggagat    1980
aaatttacaa ttttgaaaat taagcctgcg gaggatttat taagcccaga attaattaat    2040
ccgaattctt ggattacgac tccaggggct agcatttcag gaaataaact tttcattaac    2100
ttggggacaa atgggaccct tagacaaagt ctttcattaa acagttattc aacttatagt    2160
ataagcttta ctgcatcagg accatttaat gtgacggtaa gaaattctag ggaagtatta    2220
tttgaacgaa gcaaccttat gtcttcaact agtcatattt ctgggacatt caaaactgaa    2280
tccaataata ccggattata tgtagaactt tcccgtcgct ctggtggtgg tggtcatata    2340
tcatttgaaa acgtttctat taaataaaaa gg                                  2372
```

<210> SEQ ID NO 14
<211> LENGTH: 788
<212> TYPE: PRT
<213> ORGANISM: Bacillus thuringiensis

<400> SEQUENCE: 14

```
Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160
```

```
Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Phe Ser Gln Phe Ile Gly Asp Lys Leu Lys Pro Lys
```

```
                580               585              590
Thr Glu Tyr Val Ile Gln Tyr Thr Val Lys Gly Lys Pro Ser Ile His
                595               600              605
Leu Lys Asp Glu Asn Thr Gly Tyr Ile His Tyr Glu Asp Thr Asn Asn
                610               615              620
Asn Leu Lys Asp Tyr Gln Thr Ile Thr Lys Arg Phe Thr Thr Gly Thr
625             630               635                           640
Asp Leu Lys Gly Val Tyr Leu Ile Leu Lys Ser Gln Asn Gly Asp Glu
                645               650              655
Ala Trp Gly Asp Lys Phe Thr Ile Leu Glu Ile Lys Pro Ala Glu Asp
                660               665              670
Leu Leu Ser Pro Glu Leu Ile Asn Pro Asn Ser Trp Ile Thr Thr Pro
                675               680              685
Gly Ala Ser Ile Ser Gly Asn Lys Leu Phe Ile Asn Leu Gly Thr Asn
                690               695              700
Gly Thr Phe Arg Gln Ser Leu Ser Leu Asn Ser Tyr Ser Thr Tyr Ser
705             710               715                           720
Ile Ser Phe Thr Ala Ser Gly Pro Phe Asn Val Thr Val Arg Asn Ser
                725               730              735
Arg Glu Val Leu Phe Glu Arg Ser Asn Leu Met Ser Ser Thr Ser His
                740               745              750
Ile Ser Gly Thr Phe Lys Thr Glu Ser Asn Asn Thr Gly Leu Tyr Val
                755               760              765
Glu Leu Ser Arg Arg Ser Gly Gly Gly His Ile Ser Phe Glu Asn
                770               775              780
Val Ser Ile Lys
785

<210> SEQ ID NO 15
<211> LENGTH: 2367
<212> TYPE: DNA
<213> ORGANISM: Bacillus thuringiensis

<400> SEQUENCE: 15
atgaacaaga ataatactaa attaaacgca agggccctac cgagttttat tgattatttt      60
aatggcattt atggatttgc cactggtatc aaagacatta tgaatatgat ttttaaaacg     120
gatacaggtg gtaatctaac cttagacgaa atcctaaaga atcagcagtt actaaatgag     180
atttctggta aattggatgg ggtaaatggg agcttaaatg atcttatcgc acagggaaac     240
ttaaatacag aattatctaa ggaaatctta aaaattgcaa atgaacagaa tcaagtctta     300
aatgatgtta ataacaaact cgatgcgata aatacgatgc ttcatatata tctacctaaa     360
attacatcta tgttaagtga tgtaatgaag caaaattatg cgctaagtct gcaaatagaa     420
tacttaagta agcaattgca agaaatttct gataaattag atattattaa cgtaaatgtt     480
cttattaact ctacacttac tgaaattaca cctgcatatc aacggattaa atatgtgaat     540
gaaaaatttg aagaattaac ttttgctaca gaaaccactt taaaagtaaa aaaggatagc     600
tcgcctgctg atattcttga tgagttaact gaattaactg aactagcgaa aagtgttaca     660
aaaaatgacg ttgatggttt tgaattttac cttaatacat ccacgatgt aatggtagga     720 aataatttat tcgggcgttc agctttaaaa actgcttcag aattaattgc taagaaaat     780 gtgaaaacaa gtggcagtga agtaggaaat gtttataatt tcttaattgt attaacagct     840
ctacaagcaa aagcttttct tactttaaca acatgccgaa attattaggg cttagcagat     900
```

-continued

```
attgattata cttctattat gaatgaacat ttaaataagg aaaagagga atttagagta      960
aacatccttc ctacactttc taatactttt tctaatccta attatgcaaa agttaaagga    1020
agtgatgaag atgcaaagat gattgtggaa gctaaaccag acatgcatt ggttgggttt    1080
gaaatgagca atgattcaat cacagtatta aagtatatg aggctaagct aaaacaaaat    1140
tatcaagttg ataaggattc cttatcggag gttatttatg gtgatacgga taaattattt    1200
tgtccagatc aatctgaaca atatatattat acaaataaca tagtattccc aaatgaatat    1260
gtaattacta aaattgattt cactaaaaaa atgaaaactt taagatatga ggtaacagcg    1320
aatttttatg attcttctac aggagaaatt gacttaaata agaaaaaagt agaatcaagt    1380
gaagcggagt atagaacgtt aagtgctaat gatgatggag tgtatatgcc attaggtgtc    1440
atcagtgaaa catttttgac tccgataaat gggtttggcc tccaagctga tgaaaattca    1500
agattaatta ctttaacatg taaatcatat ttaagagaac tactgctagc aacagactta    1560
agcaataaag aaactaaatt gatcgtccca ccaagtggtt ttattagcaa tattgtagag    1620
aacgggtcca tagaagagga caatttagag ccgtggaaaa caaataataa gaatgcgtat    1680
gtagatcata caggcggagt gaatggaact aaagctttat atgttcataa ggacggagga    1740
ttttcacaat ttattggaga taagtaaaaa ccgaaaactg agtatgtaat ccaatatact    1800
gttaaaggaa aaccttctat tcatttaaaa gatgaaaata ctggatatat tcattatgaa    1860
gatacaaata taatttaaa agattatcaa actattacta aacgttttac tacaggaact    1920
gatttaaagg gagtgtattt aattttaaaa agtcaaaatg gagatgaagc ttggggagat    1980
aaatttacaa ttttagaaat taagcctgcg gaggattat taagcccaga attaattaat    2040
ccgaattctt ggattacgac tccaggggct agcatttcag gaaataaact tttcattaac    2100
ttggggacaa atgggacctt tagacaaagt ctttcattaa acagttattc aacttatagt    2160
ataagcttta ctgcatcagg accatttaat gtgacggtaa gaaattctag ggaagtatta    2220
tttgaacgaa gcaaccttat gtcttcaact agtcatattt ctgggacatt caaaactgaa    2280
tccaataata ccggattata tgtagaactt tcccgtcgct ctggtggtgg tggtcatata    2340
tcatttgaaa acgtttctat taaataa                                         2367
```

<210> SEQ ID NO 16
<211> LENGTH: 787
<212> TYPE: PRT
<213> ORGANISM: Bacillus thuringiensis

<400> SEQUENCE: 16

```
Met Asn Lys Asn Asn Thr Lys Leu Asn Ala Arg Ala Leu Pro Ser Phe
  1               5                  10                  15

Ile Asp Tyr Phe Asn Gly Ile Tyr Gly Phe Ala Thr Gly Ile Lys Asp
                 20                  25                  30

Ile Met Asn Met Ile Phe Lys Thr Asp Thr Gly Gly Asn Leu Thr Leu
         35                  40                  45

Asp Glu Ile Leu Lys Asn Gln Gln Leu Leu Asn Glu Ile Ser Gly Lys
     50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asn Ala Ile Asn Thr
                100                 105                 110
```

```
Met Leu His Ile Tyr Leu Pro Lys Ile Thr Ser Met Leu Asn Asp Val
            115                 120                 125
Met Lys Gln Asn Tyr Ala Leu Ser Leu Gln Ile Glu Tyr Leu Ser Lys
            130                 135                 140
Gln Leu Gln Glu Ile Ser Asp Lys Leu Asp Val Ile Asn Val Asn Val
145                 150                 155                 160
Leu Ile Asn Ser Thr Leu Thr Glu Ile Thr Pro Ala Tyr Gln Arg Met
            165                 170                 175
Lys Tyr Val Asn Glu Lys Phe Glu Asp Leu Thr Phe Ala Thr Glu Thr
            180                 185                 190
Thr Leu Lys Val Lys Lys Asn Ser Ser Pro Ala Asp Ile Leu Asp Glu
            195                 200                 205
Leu Thr Glu Leu Thr Glu Leu Ala Lys Ser Val Thr Lys Asn Asp Val
            210                 215                 220
Asp Gly Phe Glu Phe Tyr Leu Asn Thr Phe His Asp Val Met Val Gly
225                 230                 235                 240
Asn Asn Leu Phe Gly Arg Ser Ala Leu Lys Thr Ala Ser Glu Leu Ile
            245                 250                 255
Ala Lys Glu Asn Val Lys Thr Ser Gly Ser Glu Val Gly Asn Val Tyr
            260                 265                 270
Asn Phe Leu Ile Val Leu Thr Ala Leu Gln Ala Lys Ala Phe Leu Thr
            275                 280                 285
Leu Thr Thr Cys Arg Lys Leu Leu Gly Leu Ala Asp Ile Asp Tyr Thr
            290                 295                 300
Phe Ile Met Asn Glu His Leu Asp Lys Glu Lys Glu Phe Arg Val
305                 310                 315                 320
Asn Ile Leu Pro Thr Leu Ser Asn Thr Phe Ser Asn Pro Asn Tyr Ala
            325                 330                 335
Lys Ala Lys Gly Ser Asn Glu Asp Ala Lys Ile Ile Val Glu Ala Lys
            340                 345                 350
Pro Gly Tyr Ala Leu Val Gly Phe Glu Met Ser Asn Asp Ser Ile Thr
            355                 360                 365
Val Leu Lys Ala Tyr Gln Ala Lys Leu Lys Gln Asp Tyr Gln Val Asp
            370                 375                 380
Lys Asp Ser Leu Ser Glu Ile Val Tyr Gly Asp Met Asp Lys Leu Leu
385                 390                 395                 400
Cys Pro Asp Gln Ser Glu Gln Ile Tyr Tyr Thr Asn Asn Ile Ala Phe
            405                 410                 415
Pro Asn Glu Tyr Val Ile Thr Lys Ile Thr Phe Thr Lys Lys Met Asn
            420                 425                 430
Ser Leu Arg Tyr Glu Ala Thr Ala Asn Phe Tyr Asp Ser Ser Thr Gly
            435                 440                 445
Asp Ile Asp Leu Asn Lys Thr Lys Val Glu Ser Ser Glu Ala Glu Tyr
            450                 455                 460
Ser Thr Leu Ser Ala Ser Thr Asp Gly Val Tyr Met Pro Leu Gly Ile
465                 470                 475                 480
Ile Ser Glu Thr Phe Leu Thr Pro Ile Asn Gly Phe Gly Ile Val Val
            485                 490                 495
Asp Glu Asn Ser Lys Leu Val Asn Leu Thr Cys Lys Ser Tyr Leu Arg
            500                 505                 510
Glu Val Leu Leu Ala Thr Asp Leu Ser Asn Lys Glu Thr Lys Leu Ile
            515                 520                 525
Val Pro Pro Ile Gly Phe Ile Ser Asn Ile Val Glu Asn Gly Asn Leu
```

Glu Gly Glu Asn Leu Glu Pro Trp Lys Ala Asn Asn Lys Asn Ala Tyr
545                 550                 555                 560

Val Asp His Thr Gly Val Asn Gly Thr Lys Ala Leu Tyr Val His
            565                 570                 575

Lys Asp Gly Glu Phe Ser Gln Phe Ile Gly Asp Lys Leu Lys Ser Lys
                580                 585                 590

Thr Glu Tyr Val Ile Gln Tyr Ile Val Lys Gly Lys Ala Ser Ile Leu
            595                 600                 605

Leu Lys Asp Glu Lys Asn Gly Asp Cys Ile Tyr Glu Asp Thr Asn Asn
610                 615                 620

Gly Leu Glu Asp Phe Gln Thr Ile Thr Lys Ser Phe Ile Thr Gly Thr
625                 630                 635                 640

Asp Ser Ser Gly Val His Leu Ile Phe Asn Ser Gln Asn Gly Asp Glu
            645                 650                 655

Ala Phe Gly Glu Asn Phe Thr Ile Ser Glu Ile Arg Leu Ser Glu Asp
            660                 665                 670

Leu Leu Ser Pro Glu Leu Ile Asn Ser Asp Ala Trp Val Gly Ser Gln
            675                 680                 685

Gly Thr Trp Ile Ser Gly Asn Ser Leu Thr Ile Asn Ser Asn Val Asn
690                 695                 700

Gly Thr Phe Arg Gln Asn Leu Ser Leu Glu Ser Tyr Ser Thr Tyr Ser
705                 710                 715                 720

Met Asn Phe Asn Val Asn Gly Phe Ala Lys Val Thr Val Arg Asn Ser
            725                 730                 735

Arg Glu Val Leu Phe Glu Lys Asn Tyr Pro Gln Leu Ser Pro Lys Asp
            740                 745                 750

Ile Ser Glu Lys Phe Thr Thr Ala Ala Asn Asn Thr Gly Leu Tyr Val
            755                 760                 765

Glu Leu Ser Arg Phe Thr Ser Gly Gly Ala Ile Asn Phe Arg Asn Phe
770                 775                 780

Ser Ile Lys
785

<210> SEQ ID NO 17
<211> LENGTH: 2364
<212> TYPE: DNA
<213> ORGANISM: Bacillus thuringiensis

<400> SEQUENCE: 17
atgaacaaga ataatactaa attaaacgca agggccttac cgagttttat tgattatttt      60
aatggcattt atggatttgc cactggtatc aaagacatta tgaacatgat ttttaaaacg     120
gatacaggtg gaaatctaac cctagacgaa attttaaaaa atcagcagtt attaaatgag     180
atttctggta aattggatgg ggtaaatggg agcttaaacg atcttatcgc acagggaaac     240
ttaaatacag aattatctaa ggaaatctta aaaattgcaa atgagcagaa tcaagtctta     300
aatgatgtta ataacaaact taatgcgata atacaatgc ttcacatata tctacctaaa     360
attacatcta tgttaaatga tgtaatgaaa caaaattatg cactaagtct gcaaatagaa     420
tacctaagta acaattgca agaaatttcc gacaagttag atgtcattaa cgtgaatgta     480
cttattaact ctacacttac tgaaattaca cctgcgtatc aacggatgaa atatgtaaat     540
gaaaaatttg aagatttaac ttttgctaca gaaaccactt taaagtaaaa aagaatagc      600 tcccctgcag atattcttga tgagttaact gagttaactg aactagcgaa agtgtaaca      660

```
aaaaatgacg tggatggttt tgaattttac cttaatacat tccacgatgt aatggtagga      720
aacaatttat tcgggcgttc agctttaaaa actgcttcgg aattaatcgc taaagaaaat      780
gtgaaaacaa gtggcagtga ggtaggaaat gtttataatt tcttaattgt attaacagct      840
ctgcaagcaa aagcttttct tactttaaca acatgccgga aattattagg cttagcagat      900
attgattata ctttcattat gaatgaacat ttagataagg aaaagagga atttagagta      960 aatatccttc ctacactttc taatactttt tctaatccta actatgcaaa agctaaagga     1020
agcaatgaag atgcaaagat aattgtggaa gctaaaccag atatgctttt ggttggattt     1080
gaaatgagca atgattcaat cacagtatta aaagcatatc aggctaagct aaaacaagat     1140
tatcaagttg ataaagattc gttatcagaa attgtctatg gtgatatgga taattattg      1200 tgcccggatc aatctgaaca atatatatt acaaataaca ttgcttttcc caatgaatat      1260
gtaattacta aaattacttt tactaaaaaa atgaatagtt aagatatga ggcaacagct      1320 aattttatg attcttctac agggatatt gatctaaata agacaaaagt agaatcaagt      1380
gaagcagagt atagtacgct aagtgctagt actgatggag tctatatgcc gttaggtatt     1440
atcagtgaaa catttttgac tccaattaat gggtttggaa tcgtagtcga tgaaaattca     1500
aaattagtaa atttaacatg taaatcatat ttaagagagg tattattagc aacagactta     1560
agtaataaag aaactaaatt gattgtccca cctattggtt ttattagcaa tattgtagaa     1620
aatgggaact tagagggaga aaacttagag ccgtggaaag caaataacaa aaatgcgtat     1680
gtagatcata caggcggcgt aaatggaact aaagctttat atgttcataa ggatggtgag     1740
ttttcacaat ttattggaga taagttgaaa tcgaaaacag aatatgtaat tcaatatatt     1800
gtaaagggaa aagcttctat tcttttgaaa gatgaaaaaa atggtgattg catttatgaa     1860
gatacaaata atggtttaga agattttcaa accattacta aaagttttat tacaggaacg     1920
gattcttcag gagttcattt aatatttaat agtcaaaatg cgatgaagc atttggggaa     1980 aactttacta tttcagaaat taggctttcc gaagatttat taagtccaga attgataaat     2040
tcagatgctt gggttggatc tcagggaact tggatctcag gaaattcact cactattaat     2100
agtaatgtga atgaactttt tcgacaaaac ctttcgttag aaagctattc aacttatagt     2160 atgaactta tgtgaatgg atttgccaag gtgacagtaa gaaattcccg tgaagtatta      2220
tttgaaaaaa attatccgca gctttcacct aaagatattt ctgaaaaatt cacaactgca     2280
gccaataata ccgggttgta tgtagagctt tctcgtttta catcgggtgg cgctataaat     2340
ttccggaatt tttcgattaa gtga                                             2364

<210> SEQ ID NO 18
<211> LENGTH: 14241
<212> TYPE: DNA
<213> ORGANISM: Artificial Sequence
<220> FEATURE:
<223> OTHER INFORMATION: source: Bacillus thuringiensis

<400> SEQUENCE: 18
attcctgtgg ttggcatgca catacaaatg gacgaacgga taaaccttt cacgcccttt        60 taaatatccg attattctaa taaacgctct tttctcttag gttacccgc caatatatcc       120 tgtcaaacac tgatagttta aactgaaggc gggaaacgac aatctgatca tgagcggaga      180
attaagggag tcacgttatg accccgcccg atgacgcggg acaagccgtt ttacgtttgg      240
aactgacaga accgcaacgc tgcaggaatt ggccgcagcg gccatttaaa tcaattgggc      300
```

```
gcgtacgtag cactagtgaa ttccggaccc aagctttggc agacaaagtg gcagacatac    360
tgtcccacaa atgaagatgg aatctgtaaa agaaaacgcg tgaaataatg cgtctgacaa    420
aggttaggtc ggctgccttt aatcaatacc aaagtggtcc ctaccacgat ggaaaaactg    480
tgcagtcggt ttggcttttt ctgacgaaca aataagattc gtggccgaca ggtgggggtc    540
caccatgtga aggcatcttc agactccaat aatggagcaa tgacgtaagg gcttacgaaa    600
taagtaaggg tagtttggga aatgtccact cacccgtcag tctataaata cttagcccct    660
ccctcattgt taagggagca aaatctcaga gagatagtcc tagagagaga aagagagcaa    720
gtagcctaga agtggatctc caccatggcc cagtccaagc acggcctgac caaggagatg    780
accatgaagt accgcatgga gggctgcgtg gacggccaca agttcgtgat caccggcgag    840
ggcatcggct accccttcaa gggcaagcag gccatcaacc tgtgcgtggt ggagggcggc    900
cccttgccct tcgccgagga catcttgtcc gccgccttca tgtacggcaa ccgcgtgttc    960
accgagtacc cccaggacat cgtcgactac ttcaagaact cctgccccgc cggctacacc    1020
tgggaccgct ccttcctgtt cgaggacggc gccgtgtgca tctgcaacgc cgacatcacc    1080
gtgagcgtgg aggagaactg catgtaccac gagtccaagt tctacggcgt gaacttcccc    1140
gccgacggcc ccgtgatgaa gaagatgacc gacaactggg agccctcctg cgagaagatc    1200
atccccgtgc caagcaggg catcttgaag ggcgacgtga gcatgtacct gctgctgaag    1260
gacggtggcc gcttgcgctg ccagttcgac accgtgtaca aggccaagtc cgtgccccgc    1320
aagatgcccg actggcactt catccagcac aagctgaccc gcgaggaccg cagcgacgcc    1380
aagaaccaga agtggcacct gaccgagcac gccatcgcct ccggctccgc cttgccctgc    1440
tctagatccc cgaatttccc cgatcgttca acatttggc aataaagttt cttaagattg    1500
aatcctgttg ccggtcttgc gatgattatc atataatttc tgttgaatta cgttaagcat    1560
gtaataatta acatgtaatg catgacgtta tttatgagat gggtttttat gattagagtc    1620
ccgcaattat acatttaata cgcgatagaa acaaaatat agcgcgcaaa ctaggataaa    1680
ttatcgcgcg cggtgtcatc tatgttacta gatcgggacc cggcgcgcca tttaaatggt    1740
accggaccca gctgcttgtg gggaccgac aaaaaaggaa tggtgcagaa ttgttaggcg    1800
cacctaccaa aagcatcttt gcctttattg caaagataaa gcagattcct ctagtacaag    1860
tggggaacaa aataacgtgg aaaagagctg tcctgacagc ccactcacta atgcgtatga    1920
cgaacgcagt gacgaccaca aaactcgaga ctttcaaca aagggtaata tccggaaacc    1980
tcctcggatt ccattgccca gctatctgtc actttattgt gaagatagtg gaaaaggaag    2040
gtggctccta caaatgccat cattgcgata aaggaaaggc tatcgttgaa gatgcctctg    2100
ccgacagtgg tcccaaagat ggacccccac ccacgaggag catcgtggaa aaagaagacg    2160
ttccaaccac gtcttcaaag caagtggatt gatgtgatat ctccactgac gtaagggatg    2220
acgaacaatc ccactatcct tctgccggac cctctagagt cgacaaaatt tagaacgaac    2280
ttaattatga tctcaaatac attgatacat atctcatcta gatctaggtt atcattatgt    2340
aagaaagttt tgacgaatat ggcacgacaa aatggctaga ctcgatgtaa ttggtatctc    2400
aactcaacat tatacttata ccaaacatta gttagacaaa atttaaacaa ctattttta    2460
tgtatgcaag agtcagcata tgtataattg attcagaatc gttttgacga gttcggatgt    2520
agtagtagcc attatttaat gtacatacta atcgtgaata gtgaatatga tgaaacattg    2580
tatcttattg tataaatatc cataaacaca tcatgaaaga cactttcttt cacggtctga    2640
attaattatg atacaattct aatagaaaac gaattaaatt acgttgaatt gtatgaaatc    2700
```

```
taattgaaca agccaaccac gacgacgact aacgttgcct ggattgactc ggtttaagtt    2760
aaccactaaa aaaacggagc tgtcatgtaa cacgcggatc gagcaggtca cagtcatgaa    2820
gccatcaaag caaagaact aatccaaggg ctgagatgat taattagttt aaaaattagt     2880
taacacgagg gaaaaggctg tctgacagcc aggtcacgtt atctttacct gtggtcgaaa    2940
tgattcgtgt ctgtcgattt taattatttt tttgaaaggc cgaaaataaa gttgtaagag    3000
ataaacccgc ctatataaat tcatatattt tcctctccgc tttgaattgt ctcgttgtcc    3060
tcctcacttt catcagccgt tttgaatctc cggcgacttg acagagaaga acaaggaaga    3120
agactaagag agaaagtaag agataatcca ggagattcat tctccgtttt gaatcttcct    3180
caatctcatc ttcttccgct cttctttcc aaggtaatag gaactttctg gatctacttt     3240
atttgctgga tctcgatctt gttttctcaa tttccttgag atctggaatt cgtttaattt    3300
ggatctgtga acctccacta aatcttttgg ttttactaga atcgatctaa gttgaccgat    3360
cagttagctc gattatagct accagaattt ggcttgacct tgatggagag atccatgttc    3420
atgttacctg ggaaatgatt tgtatatgtg aattgaaatc tgaactgttg aagttagatt    3480
gaatctgaac actgtcaatg ttagattgaa tctgaacact gtttaaggtt agatgaagtt    3540
tgtgtataga ttcttcgaaa ctttaggatt tgtagtgtcg tacgttgaac agaaagctat    3600
ttctgattca atcagggttt atttgactgt attgaactct ttttgtgtgt ttgcagctca    3660 taaaaggat ccaccatgaa caagaacaac accaagctga gcacccgcgc cctgccgagc      3720
ttcatcgact acttcaacgg catctacggc ttcgccaccg gcatcaagga catcatgaac    3780
atgatcttca agaccgacac cggcggcgac ctgacctgg acgagatcct gaagaaccag     3840
cagctgctga cgacatcag cggcaagctg gacggcgtga acggcagcct gaacgacctg     3900
atcgcccagg gcaacctgaa caccgagctg agcaaggaga tccttaagat cgccaacgag    3960
cagaaccagg tgctgaacga cgtgaacaac aagctggacg ccatcaacac catgctgcgc    4020
gtgtacctgc cgaagatcac cagcatgctg agcgacgtga ttaagcagaa ctacgccctg    4080
agcctgcaga tcgagtacct gagcaagcag ctgcaggaga tcagcgacaa gctggacatc    4140
atcaacgtga acgtcctgat caacagcacc ctgaccgaga tcaccccggc ctaccagcgc    4200
atcaagtacg tgaacgagaa gttcgaagag ctgaccttcg ccaccgagac cagcagcaag    4260
gtgaagaagg acggcagccc ggccgacatc ctggacgagc tgaccgagct gaccgagctg    4320
gcgaagagcg tgaccaagaa cgacgtggac ggcttcgagt tctacctgaa caccttccac    4380
gacgtgatgg tgggcaacaa cctgttcggc cgcagcgccc tgaagaccgc cagcgagctg    4440
atcaccaagg agaacgtgaa gaccagcggc agcgaggtgg gcaacgtgta caacttcctg    4500
atcgtgctga ccgccctgca ggcccaggcc ttcctgaccc tgaccacctg tcgcaagctg    4560
ctgggcctgg ccgacatcga ctacaccagc atcatgaacg agcacttgaa caaggagaag    4620
gaggagttcc gcgtgaacat cctgccgacc ctgagcaaca ccttcagcaa cccgaactac    4680
gccaaggtga agggcagcga cgaggacgcc aagatgatcg tggaggctaa gccgggccac    4740
gcgttgatcg gcttcgagat cagcaacgac agcatcaccg tgctgaaggt gtacgaggcc    4800
aagctgaagc agaactacca ggtggacaag gacagcttga gcgaggtgat ctacggcgac    4860
atggacaagc tgctgtgtcc ggaccagagc gagcaaatct actacaccaa caacatcgtg    4920
ttcccgaacg agtacgtgat caccaagatc gacttcacca agaagatgaa gaccctgcgc    4980
tacgaggtga ccgccaactt ctacgacagc agcaccggcg agatcgacct gaacaagaag    5040
```

```
aaggtggaga gcagcgaggc cgagtaccgc accctgagcg cgaacgacga cggcgtctac    5100
atgccactgg gcgtgatcag cgagaccttc ctgaccccga tcaacggctt tggcctgcag    5160
gccgacgaga acagccgcct gatcaccctg acctgtaaga gctacctgcg cgagctgctg    5220
ctagccaccg acctgagcaa caaggagacc aagctgatcg tgccaccgag cggcttcatc    5280
agcaacatcg tggagaacgg cagcatcgag gaggacaacc tggagccgtg aaggccaac    5340 aacaagaacg cctacgtcga ccacaccggc ggcgtgaacg gcaccaaggc cctgtacgtg    5400
cacaaggacg gcggcatcag ccagttcatc ggcgacaagc tgaagccgaa gaccgagtac    5460
gtgatccagt acaccgtgaa gggcaagcca tcgattcacc tgaaggacga gaacaccggc    5520
tacatccact acgaggacac caacaacaac ctggaggact accagaccat caacaagcgc    5580
ttcaccaccg gcaccgacct gaagggcgtg tacctgatcc tgaagagcca gaacggcgac    5640
gaggcctggg gcgacaactt catcatcctg gagatcagcc cgagcgagaa gctgctgagc    5700
ccggagctga tcaacaccaa caactggacc agcaccggca gcaccaacat cagcggcaac    5760
accctgaccc tgtaccaggg cggccgcggc atcctgaagc agaacctgca gctggacagc    5820
ttcagcacct accgcgtgta cttcagcgtg agcggcgacg ccaacgtgcg catccgcaac    5880
tcccgcgagg tgctgttcga gaagaggtac atgagcggcg ccaaggacgt gagcgagatg    5940
ttcaccacca agttcgagaa ggacaacttc tacatcgagc tgagccaggg caacaacctg    6000
tacggcggcc cgatcgtgca cttctacgac gtgagcatca gtaggagct cttcatatga    6060 cgatcgttca acatttggc aataaagttt cttaagattg aatcctgttg ccggtcttgc    6120
gatgattatc atataatttc tgttgaatta cgttaagcat gtaataatta acatgtaatg    6180
catgacgtta tttatgagat gggtttttat gattagagtc ccgcaattat acatttaata    6240
cgcgataaga aacaaaatat agcgcgcaaa ctaggataaa ttatcgcgcg cggtgtcatc    6300
tatgttacta gatcgcggac cctagcggac cgaagcttgc atgcctgcag gtcgactcta    6360
gaggaaccgg agccaagtct cataaacgcc attgtggaag aaagtcttga gttggtggta    6420
atgtaacaga gtagtaagaa cagagaagag agagagtgtg agatacatga attgtcgggc    6480
aacaaaaatc ctgaacatct tattttagca aagagaaaga gttccgagtc tgtagcagaa    6540
gagtgaggag aaatttaagc tcttggactt gtgaattgtt ccgcctcttg aatacttctt    6600
caatcctcat atattcttct tctatgttac ctgaaaaccg gcatttaatc tcgcgggttt    6660
attccggttc aacatttttt ttgttttgag ttattatctg ggcttaataa cgcaggcctg    6720
aaataaattc aaggcccaac tgtttttttt tttaagaagt tgctgttaaa aaaaaaaaa    6780 gggaattaac aacaacaaca aaaaagata aagaaaataa taacaattac tttaattgta    6840
gactaaaaaa acatagattt tatcatgaaa aaaagagaaa agaaataaaa acttggatca    6900
aaaaaaaaac atacagatct tctaattatt aacttttctt aaaaattagg tcctttttcc    6960
caacaattag gttagagtt ttggaattaa accaaaaaga ttgttctaaa aaatactcaa    7020
atttggtaga taagtttcct tattttaatt agtcaatggt agatactttt ttttcttttc    7080
tttattagag tagattagaa tcttttatgc caagtattga taaattaaat caagaagata    7140
aactatcata atcaacatga aattaaaaga aaaatctcat atatagtatt agtattctct    7200
atatatatta tgattgctta ttcttaatgg gttgggttaa ccaagacata gtcttaatgg    7260
aaagaatctt ttttgaactt tttccttatt gattaaattc ttctatagaa aagaaagaaa    7320
ttatttgagg aaaagtatat acaaaaagaa aaatagaaaa atgtcagtga agcagatgta    7380
atggatgacc taatccaacc accaccatag gatgtttcta cttgagtcgg tcttttaaaa    7440
```

```
acgcacggtg gaaaatatga cacgtatcat atgattcctt cctttagttt cgtgataata    7500
atcctcaact gatatcttcc ttttttttgtt ttggctaaag atattttatt ctcattaata   7560
gaaaagacgg ttttgggctt ttggtttgcg atataaagaa gaccttcgtg tggaagataa    7620
taattcatcc tttcgtcttt ttctgactct tcaatctctc ccaaagccta aagcgatctc    7680
tgcaaatctc tcgcgactct ctctttcaag gtatattttc tgattctttt tgttttttgat  7740
tcgtatctga tctccaattt ttgttatgtg gattattgaa tcttttgtat aaattgctttt   7800
tgacaatatt gttcgtttcg tcaatccagc ttctaaattt tgtcctgatt actaagatat    7860
cgattcgtag tgtttacatc tgtgtaattt cttgcttgat tgtgaaatta ggattttcaa    7920
ggacgatcta ttcaattttt gtgttttctt tgttcgattc tctctgtttt aggtttctta    7980
tgtttagatc cgtttctctt tggtgttgtt ttgattctc ttacggcttt tgatttggta     8040
tatgttcgct gattggtttc tacttgttct attgttttat ttcaggtaga tctcaccatg    8100
tctccggaga ggagaccagt tgagattagg ccagctacag cagctgatat ggccgcggtt    8160
tgtgatatcg ttaaccatta cattgagacg tctacagtga actttaggac agagccacaa    8220
acaccacaag agtggattga tgatctagag aggttgcaag atagataccc ttggttggtt    8280
gctgaggttg agggtgttgt ggctggtatt gcttacgctg ggccctggaa ggctaggaac    8340
gcttacgatt ggacagttga gagtactgtt tacgtgtcac ataggcatca aaggttgggc    8400
ctaggatcta cattgtacac acatttgctt aagtctatgg aggcgcaagg ttttaagtct    8460
gtggttgctg ttataggcct tccaaacgat ccatctgtta ggttgcatga ggctttggga    8520
tacacagccc ggggtacatt gcgcgcagct ggatacaagc atggtggatg gcatgatgtt    8580
ggttttttggc aaagggattt tgagttgcca gctcctccaa ggccagttag gccagttacc    8640
cagatatgag tcgagcgcta gatccccgaa tttccccgat cgttcaaaca tttggcaata   8700
aagtttctta agattgaatc ctgttgccgg tcttgcgatg attatcatat aatttctgtt    8760
gaattacgtt aagcatgtaa taattaacat gtaatgcatg acgttattta tgagatgggt    8820
ttttatgatt agagtcccgc aattatacat ttaatacgcg atagaaaaca aaatatagcg    8880
cgcaaactag gataaattat cgcgcgcggt gtcatctatg ttactagatc gggaattggg    8940
taccatgccc gggcggccag catggccgta tccgcaatgt gttattaagt tgtctaagcg    9000
tcaatttgtt tacaccacaa tatatcctgc caccagccag ccaacagctc cccgaccggc    9060
agctcggcac aaaatcacca ctcgatacag gcagcccatc agaattaatt ctcatgtttg    9120
acagcttatc atcgactgca cggtgcacca atgcttctgg cgtcaggcag ccatcggaag    9180
ctgtggtatg gctgtgcagg tcgtaaatca ctgcataatt cgtgtcgctc aaggcgcact   9240
cccgttctgg ataatgtttt ttgcgccgac atcataacgg ttctggcaaa tattctgaaa    9300
tgagctgttg acaattaatc atccggctcg tataatgtgt ggaattgtga gcggataaca    9360
atttcacaca ggaaacagac catgagggaa gcgttgatcg ccgaagtatc gactcaacta   9420
tcagaggtag ttggcgtcat cgagcgccat ctcgaaccga cgttgctggc cgtacatttg    9480
tacggctccg cagtggatgg cggcctgaag ccacacagtg atattgattt gctggttacg    9540
gtgaccgtaa ggcttgatga acaacgcgg cgagctttga tcaacgacct tttggaaact     9600
tcggcttccc ctggagagag cgagattctc cgcgctgtag aagtcaccat tgttgtgcac    9660
gacgacatca ttccgtggcg ttatccagct aagcgcgaac tgcaatttgg agaatggcag    9720
cgcaatgaca ttcttgcagg tatcttcgag ccagccacga tcgacattga tctggctatc    9780
```

```
ttgctgacaa aagcaagaga acatagcgtt gccttggtag gtccagcggc ggaggaactc      9840
tttgatccgg ttcctgaaca ggatctattt gaggcgctaa atgaaacctt aacgctatgg      9900
aactcgccgc ccgactgggc tggcgatgag cgaaatgtag tgcttacgtt gtcccgcatt      9960
tggtacagcg cagtaaccgg caaaatcgcg ccgaaggatg tcgctgccga ctgggcaatg     10020
gagcgcctgc cggcccagta tcagcccgtc atacttgaag ctaggcaggc ttatcttgga     10080
caagaagatc gcttggcctc gcgcgcagat cagttggaag aatttgttca ctacgtgaaa     10140
ggcgagatca ccaaagtagt cggcaaataa agctctagtg gatctccgta cccggggatc     10200
tggctcgcgg cggacgcacg acgccggggc gagaccatag gcgatctcct aaatcaatag     10260
tagctgtaac ctcgaagcgt ttcacttgta acaacgattg agaattttg tcataaaatt      10320 gaaatacttg gttcgcattt ttgtcatccg cggtcagccg caattctgac gaactgccca     10380
tttagctgga gatgattgta catccttcac gtgaaaattt ctcaagcgca gtgaacaagg     10440
gttcagattt tagattgaaa ggtgagccgt tgaaacacgt tcttcttgtc gatgacgacg     10500
tcgctatgcg gcatcttatt attgaatacc ttacgatcca cgccttcaaa gtgaccgcgg     10560
tagccgacag cacccagttc acaagagtac tctcttccgc gacggtcgat gtcgtggttg     10620
ttgatctaga tttaggtcgt gaagatgggc tcgagatcgt tcgtaatctg gcggcaaagt     10680
ctgatattcc aatcataatt atcagtggcg accgccttga ggagacggat aaagttgttg     10740
cactcgagct aggagcaagt gattttatcg ctaagccgtt cagtatcaga gagtttctag     10800
cacgcattcg ggttgccttg cgcgtgcgcc ccaacgttgt ccgctccaaa gaccgacggt     10860 cttttgttt tactgactgg acacttaatc tcaggcaacg tcgcttgatg tccgaagctg      10920
gcggtgaggt gaaacttacg gcaggtgagt tcaatcttct cctcgcgttt ttagagaaac     10980
cccgcgacgt tctatcgcgc gagcaacttc tcattgccag tcgagtacgc gacgaggagg     11040
tttatgacag gagtatagat gttctcattt tgaggctgcg ccgcaaactt gaggcagatc     11100
cgtcaagccc tcaactgata aaaacagcaa gaggtgccgg ttatttcttt gacgcggacg     11160
tgcaggtttc gcacgggggg acgatggcag cctgagccaa ttcccagatc cccgaggaat     11220
cggcgtgagc ggtcgcaaac catccggccc ggtacaaatc ggcgcggcgc tgggtgatga     11280
cctggtggag aagttgaagg ccgcgcaggc cgcccagcgg caacgcatcg aggcagaagc     11340 acgcccggt gaatcgtggc aagcggccgc tgatcgaatc cgcaaagaat cccggcaacc      11400
gccggcagcc ggtgcgccgt cgattaggaa gccgcccaag ggcgacgagc aaccagattt     11460
tttcgttccg atgctctatg acgtgggcac ccgcgatagt cgcagcatca tggacgtggc     11520
cgttttccgt ctgtcgaagc gtgaccgacg agctggcgag gtgatccgct acgagcttcc     11580
agacgggcac gtagaggttt ccgcaggcc ggccggcatg ccagtgtgt gggattacga       11640 cctggtactg atggcggttt cccatctaac cgaatccatg aaccgatacc gggaagggaa     11700
gggagacaag cccggccgcg tgttccgtcc acacgttgcg gacgtactca agttctgccg     11760
gcgagccgat ggcggaaagc agaaagacga cctggtagaa acctgcattc ggttaaacac     11820
cacgcacgtt gccatgcagc gtacgaagaa ggccaagaac ggccgcctgg tgacggtatc     11880
cgagggtgaa gccttgatta ccgctacaa gatcgtaaag agcgaaaccg gcggccgga       11940 gtacatcgag atcgagctag ctgattggat gtaccgcgag atcacagaag gcaagaaccc     12000
ggacgtgctg acggttcacc ccgattactt tttgatcgat cccggcatcg gccgttttct     12060
ctaccgcctg gcacgccgcg ccgcaggcaa ggcagaagcc agatggttgt tcaagacgat     12120
ctacgaacgc agtggcagcg ccggagagtt caagaagttc tgtttcaccg tgcgcaagct     12180
```

```
gatcgggtca aatgacctgc cggagtacga tttgaaggag gaggcggggc aggctggccc    12240
gatcctagtc atgcgctacc gcaacctgat cgagggcgaa gcatccgccg gttcctaatg    12300
tacggagcag atgctagggc aaattgccct agcagggga aaaggtcgaa aaggtctctt     12360
tcctgtggat agcacgtaca ttgggaaccc aaagccgtac attgggaacc ggaacccgta    12420
cattgggaac ccaaagccgt acattgggaa ccggtcacac atgtaagtga ctgatataaa    12480
agagaaaaaa ggcgattttt ccgcctaaaa ctctttaaaa cttattaaaa ctcttaaaac    12540
ccgcctggcc tgtgcataac tgtctggcca gcgcacagcc gaagagctgc aaaaagcgcc    12600 taccctttcgg tcgctgcgct ccctacgccc cgccgcttcg cgtcggccta tcgcggccgc   12660
tggccgctca aaatggctg gcctacggcc aggcaatcta ccagggcgcg acaagccgc      12720 gccgtcgcca ctcgaccgcc ggcgctgagg tctgcctcgt gaagaaggtg ttgctgactc    12780
ataccaggcc tgaatcgccc catcatccag ccagaaagtg agggagccac ggttgatgag    12840
agctttgttg taggtggacc agttggtgat tttgaactt tgctttgcca cggaacggtc     12900
tgcgttgtcg ggaagatgcg tgatctgatc cttcaactca gcaaaagttc gatttattca    12960
acaaagccgc cgtcccgtca agtcagcgta atgctctgcc agtgttacaa ccaattaacc    13020
aattctgatt agaaaaactc atcgagcatc aaatgaaact gcaatttatt catatcagga    13080
ttatcaatac catattttg aaaaagccgt ttctgtaatg aaggagaaaa ctcaccgagg      13140
cagttccata ggatggcaag atcctggtat cggtctgcga ttccgactcg tccaacatca    13200
atacaaccta ttaatttccc ctcgtcaaaa ataaggttat caagtgagaa atcaccatga    13260
gtgacgactg aatccggtga aatggcaaaa agctctgcat taatgaatcg gccaacgcgc    13320
ggggagaggc ggtttgcgta ttgggcgctc ttccgcttcc tcgctcactg actcgctgcg    13380
ctcggtcgtt cggctgcggc gagcggtatc agctcactca aaggcggtaa tacggttatc    13440
cacagaatca ggggataacg caggaaagaa catgtgagca aaaggccagc aaaaggccag    13500
gaaccgtaaa aaggccgcgt tgctggcgtt tttccatagg ctccgccccc ctgacgagca    13560
tcacaaaaat cgacgctcaa gtcagaggtg gcgaaacccg acaggactat aaagatacca    13620
ggcgtttccc cctggaagct ccctcgtgcg ctctcctgtt ccgaccctgc cgcttaccgg    13680
atacctgtcc gcctttctcc cttcgggaag cgtggcgctt tctcatagct cacgctgtag    13740
gtatctcagt tcggtgtagg tcgttcgctc caagctgggc tgtgtgcacg aaccccccgt    13800
tcagcccgac cgctgcgcct tatccggtaa ctatcgtctt gagtccaacc cggtaagaca    13860
cgacttatcg ccactggcag cagccactgg taacaggatt agcagagcga ggtatgtagg    13920
cggtgctaca gagttcttga agtggtggcc taactacggc tacactagaa gaacagtatt    13980
tggtatctgc gctctgctga agccagttac cttcggaaaa agagttggta gctcttgatc    14040
cggcaaacaa accaccgctg gtagcggtgg tttttttgtt tgcaagcagc agattacgcg    14100
cagaaaaaaa ggatctcaag aagatccttt gatcttttct acggggtctg acgctcagtg    14160
gaacgaaaac tcacgttaag ggattttggt catgagatta tcaaaaagga tcttcaccta    14220
gatccttttg atccggaatt a                                              14241
```

<210> SEQ ID NO 19

```
<211> LENGTH: 11
<212> TYPE: PRT
<213> ORGANISM: Bacillus thuringiensis

<400> SEQUENCE: 19

Ile Tyr Gly Phe Ala Thr Gly Ile Lys Asp Ile
1               5                   10
```

METHODS AND COMPOSITIONS FOR CONTROLLING NEMATODE PESTS

RELATED APPLICATION INFORMATION

This application claims priority under 35 U.S.C. §371 from PCT Application No. PCT/US2012/046239, filed Jul. 11, 2012, which claims the benefit of United States Provisional Application No. 61/512,575, filed Jul. 28, 2011, the disclosures of which are incorporated by reference herein in their entirety.

FIELD OF THE INVENTION

The invention relates to methods for preventing or controlling nematode infestation of plants. More particularly, the invention relates to the control of nematode pests in plants using vegetative insecticidal proteins. The invention also relates to transgenic plants tolerant or resistant to nematode infestation.

BACKGROUND

Plant pests are a major factor in the loss of the world's important agricultural crops. About $8 billion are lost every year in the U.S. alone due to infestations of invertbrate pests including nematodes. In addition to losses in field crops, nematode pests are also a burden to vegetable and fruit growers, to producers of ornamental flowers, and to home gardeners. Plant-infesting nematodes, a majority of which are root feeders, are found in association with most plants. Some are endoparasitic, living and feeding within the tissue of the roots, tubers, buds, seeds, etc. Others are ectoparasitic, feeding externally through plant walls. A single endoparasitic nematode can kill a plant or reduce its productivity. Endoparasitic root feeders include such economically important pests as the root-knot nematodes (*Meloidogyne* species), the reniform nematodes (*Rotylenchulus* species), the cyst nematodes (*Heterodera* species), and the root-lesion nematodes (*Pratylenchus* species). Direct feeding by nematodes can drastically decrease a plant's uptake of nutrients and water. Nematodes have the greatest impact on crop productivity when they attack the roots of seedlings immediately after seed germination. Nematode feeding also creates open wounds that provide entry to a wide variety of plant-pathogenic fungi and bacteria. These microbial infections can be more economically damaging than the direct effects of nematode feeding.

Cyst nematodes are responsible for direct loss in soybean yield and indirect loss due to cost of pesticides and non-optimal use of land for rotation. Soybean cyst nematode (*Heterodera glycines*) has a negative economic impact that may exceed $1 billion per year in North America. Economically significant densities of cyst nematodes usually cause stunting of crop plants. The stunted plants have smaller root systems, show symptoms of mineral deficiencies in their leaves, and wilt easily.

Traditional practices for managing nematode infestations include maintaining proper fertility and soil pH levels in nematode-infested land; controlling plant diseases that aid nematode invasion, as well as controlling insect and weed pests; using sanitation practices such as plowing, planting, and cultivating of nematode-infested fields only after working non-infested fields; cleaning equipment thoroughly after working in infested fields; not using seed from plants grown on infested land for planting non-infested fields unless the seed has been properly cleaned; rotating infested fields and alternating host crops with non-host crops, such as, corn, oat and alfalfa and planting resistant or tolerant plant varieties. While many of these can be effective they are time consuming and costly to implement. Nematodes are difficult pests to control without the use of chemical pesticides or fumigants (e.g., nematicides), and the availability of these nematicides is decreasing due to high toxicity to humans and the environment. Furthermore, under the Montreal Protocol of 1987, one of the main chemicals used to control nematode infestation, methyl bromide, has been phased out. Thus, there is currently no efficient and effective approach to control nematode infestation of plants.

Biological pest control agents, such as *Bacillus thuringiensis* strains expressing pesticidal toxins like delta-endotoxins (also called Cry proteins), have been applied to crop plants with satisfactory results, offering an alternative or compliment to chemical pesticides. Some Cry proteins, for example Cry1, Cry 5, Cry6, Cry11, Cry12, Cry13, Cry14, Cry21 and Cry22, have been shown to provide some activity against certain nematode species in laboratory bioassays. However, control of nematode pests by expression of Cry proteins in plants has not been demonstrated, particularly in field crops such as soybean or corn.

Other, non-endotoxin genes and the insecticidal proteins they encode have also been identified. U.S. Pat. Nos. 5,877,012, 6,107,279, 6,137,033, and 6,291,156, as well as Estruch et al. (1996, Proc. Natl. Acad. Sci. 93:5389-5394) and Yu et al. (1997, Appl. Environ. Microbiol. 63:532-536), describe a new class of insecticidal proteins called. Vip3 (vegetative insecticidal protein 3). Vip3 genes encode approximately 88 kDa proteins that are produced and secreted by *Bacillus* during its vegetative stage of growth (vegetative insecticidal proteins, VIP). For example, one family of the Vip3 protein class, called Vip3A, possesses insecticidal activity against a wide spectrum of lepidopteran pests, including, but not limited to, black cutworm (BCW, *Agrotis ipsilon*), fall armyworm (FAW, *Spodoptera frugiperda*), tobacco budworm (TBW, *Heliothis virescens*), and corn earworm (CEW, *Helicoverpa zea*). More recently, plants expressing the Vip3A protein have been found to be resistant to feeding damage caused by hemipteran insect pests (U.S. Pat. No. 6,429,360). Thus, Vip3A proteins display a unique spectrum of insecticidal activities. Other disclosures, WO 98/18932, WO 98/33991, WO 98/00546, and WO 99/57282, have also now identified homologues of the Vip3 class of proteins. Proteins from the Vip3 class have heretofore not been shown to have any activity against non-insect pests such as nematodes.

Due to the above described limitations in the art, there remains a need to develop new methods for controlling nematode plant pests that provide an economic benefit to farmers and that are environmentally acceptable.

SUMMARY

The needs outlined above are met by the invention which, in various embodiments, provides new methods of controlling economically important nematode pests. In particular, transgenic plants and/or plant parts expressing the vegetative insecticidal protein, Vip3, were surprisingly found to be capable of inhibiting the ability of nematode pests to survive, grow and reproduce, or of limiting nematode-related damage or loss to crop plants. The invention is further drawn to transgenic nematode-resistant plants which express a Vip3 protein and to methods of using the transgenic plants alone or in combination with other nematode control strategies to confer maximal nematode control efficiency with minimal environmental impact. Plants and plant parts expressing a Vip3 protein are highly tolerant or resistant to nematode infestation. For example, the economically important nematode pest, soybean cyst nematode (*Heterodera glycines*) can be controlled by transgenic soybean plants which express a Vip3A protein.

According to one aspect, the invention provides a method of controlling a nematode pest comprising contacting the nematode pest with a Vip3 protein comprising SEQ ID NO: 19. In another aspect, the Vip3 protein can be a Vip3A protein, for example, SEQ ID NO:1 or a nematode-active Vip3A protein homologue having at least about 82% identity with SEQ ID NO: 1.

According to one aspect, the invention provides a method of controlling a nematode pest, comprising contacting the nematode pest with a transgenic plant or plant part comprising a heterologous nucleic acid molecule that directs expression of a Vip3 protein of the invention in the transgenic plant or plant part, wherein the transgenic plant or plant part controls the nematode pest compared to a plant or plant part of the same type that does not express the Vip3 protein.

In another aspect of the invention, the nematode pest is selected from the group consisting of *Criconemella, Ditylenchus, Globodera, Helicotylenchus, Heterodera, Longidorus, Meloidogyne, Paratrichodorus, Pratylenchus, Radolpholus, Rotelynchus, Rotylenchulus, Tylenchulus* and *Xiphinema*. Such nematode pests selected from these genera can be cyst-forming nematodes. In another aspect, the cyst-forming nematodes are in the genus *Heterodera*. In yet another aspect, the nematode pest is *Heterodera glycines* (soybean cyst nematode).

In another aspect of the invention, the transgenic plant or plant part is selected from the group consisting of alfalfa, apple, apricot, *Arabidopsis*, artichoke, asparagus, avocado, banana, barley, beans, beet, blackberry, blueberry, *Brassica*, broccoli, Brussels sprouts, cabbage, canola, carrot, cassava, cauliflower, a cereal, celery, cherry, citrus, Clementine, coffee, corn, cotton, cucumber, eggplant, endive, eucalyptus, figs, grape, grapefruit, groundnuts, ground cherry, kiwifruit, lettuce, leek, lemon, lime, pine, maize, mango, melon, millet, mushroom, nut oat, okra, onion, orange, an ornamental plant or flower or tree, papaya, parsley, pea, peach, peanut, peat, pepper, persimmon, pineapple, plantain, plum, pomegranate, potato, pumpkin, radicchio, radish, rapeseed, raspberry, rice, rye, sorghum, soy, soybean, spinach, strawberry, sugar beet, sugarcane, sunflower, sweet potato, tangerine, tea, tobacco, tomato, a vine, watermelon, wheat, yams and zucchini. In still another aspect, the transgenic plant or plant part is a soybean plant or plant part.

In another aspect of the invention, the plant part is a root. In still another aspect, the root is a soybean root.

In yet another aspect of the invention, the Vip3 protein is a Vip3A protein. In still another aspect, the Vip3A protein comprises an amino acid sequence that is the translation product of a nucleotide sequence whose complement hybridizes to SEQ ID NO: 2, SEQ ID NO: 4, SEQ ID NO: 5, SEQ ID NO: 7, SEQ ID NO: 9, SEQ ID NO: 11, SEQ ID NO: 13, SEQ ID NO: 15 or SEQ ID NO: 17 under high-stringency conditions.

In another aspect, the Vip3 protein of the invention is selected from the group consisting of Vip3Aa1 (AAC37036), Vip3Aa2 (AAC37037), Vip3Aa3 (U.S. Pat. No. 6,137,033), Vip3Aa4 (AAR81079), Vip3Aa5 (AAR81080), Vip3Aa6 (AAR81081), Vip3Aa7 (AAK95326), Vip3Aa8 (AAK97481), Vip3Aa9 (CAA76665), Vip3Aa10 (AAN60738), Vip3Aa11 (AAR36859), Vip3Aa12 (AAM22456), Vip3Aa13 (AAL69542), Vip3Aa14 (AAQ12340), Vip3Aa15 (AAP51131), Vip3Aa16 (AAW65132), Vip3Aa17 (U.S. Pat. No. 6,603,063), Vip3Aa18 (AAX49395), Vip3Aa19 (DQ241674), Vip3Aa19 (DQ539887), Vip3Aa20 (DQ539888), Vip3Aa21 (ABD84410), Vip3Aa22 (AAY41427), Vip3Aa23 (AAY41428), Vip3Aa24 (BI 880913), Vip3Aa25 (EF608501), Vip3Aa26 (EU294496), Vip3Aa27 (EU332167), Vip3Aa28 (FJ494817), Vip3Aa29 (FJ626674), Vip3Aa30 (FJ626675), Vip3Aa31 (FJ626676), Vip3Aa32 (FJ626677), Vip3Aa33 (GU073128), Vip3Aa34 (GU073129), Vip3Aa35 (GU733921), Vip3Aa36 (GU951510), Vip3Aa37 (HM132041), Vip3Aa38 (HM117632), Vip3Aa39 (HM117631), Vip3Aa40 (HM132042), Vip3Aa41 (HM132043), Vip3Aa42 (HQ587048), Vip3Aa43 (HQ594534), Vip3Aa44 (HQ650163), Vip3Ab1 (AAR40284), Vip3Ab2 (AAY88247), Vip3Ac1 (US Patent Application Publication 20040128716), Vip3Ad1 (US Patent Application Publication 20040128716), Vip3Ad2 (CAI43276), Vip3Ae1 (CAI43277), Vip3Af1 (CAI43275), Vip3Af2 (ADN08753), Vip3Af3 (HM117634), Vip3Ag1 (ADN08758), Vip3Ag2 (FJ556803), Vip3Ag3 (HM117633), Vip3Ag4 (HQ414237), Vip3Ag5 (HQ542193), and Vip3Ah1 (DQ832323).

In another aspect, a Vip3A protein of the invention comprises SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16, or a nematode-active homologue thereof having at least 80%, 81%, 82%, 83%, 84%, 85%, 86%, 87%, 88%, 89%, 90%, 91%, 92%, 93%, 94%, 95%, 96%, 97%, 98% or 99 sequence identity with SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16. In another embodiment, the Vip3A protein comprises SEQ ID NO: 1 or a nematode-active homologue having at least 80%, 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1.

In another aspect of the invention, a transgenic plant of the invention further comprises or expresses at least one additional pesticidal agent, for example without limitation, a patatin, a *Bacillus thuringiensis* insecticidal protein, a *Bacillus thuringiensis* nematicidal protein, a *Xenorhabdus* insecticidal protein, a *Photorhabdus* insecticidal protein, a *Bacillus laterosporous* insecticidal protein, a *Bacillus sphearicus* insecticidal protein and/or an RNAi molecule that targets a nematode pest.

In another aspect, a *Bacillus thuringiensis* nematicidal protein is selected from the group consisting of a Cry1, a Cry3, a Cry11, a Cry12, a Cry13, a Cry14, a Cry21, and a Cry22.

According to another aspect, the invention provides a method of conferring nematode resistance to a plant and/or a plant part comprising inserting in the plant and/or a plant part a heterologous nucleic acid molecule encoding a Vip3 protein, wherein the plant and/or plant part expresses the Vip3 protein at a nematode-inhibiting level so as to confer nematode resistance to the plant and/or plant part compared to the same type of plant and/or plant part not expressing the Vip3 protein. Such insertion may occur via transformation or breeding.

According to another aspect, the invention provides a method of reducing nematode infectivity to a plant and/or plant part comprising contacting the nematode with a Vip3 protein, wherein nematode infectivity is reduced compared to infectivity of a plant and/or plant part by a nematode not contacted with a Vip3 protein.

In yet another aspect, the invention provides a transgenic soybean plant or plant part thereof comprising a heterologous nucleic acid molecule encoding a Vip3 protein, wherein the transgenic soybean plant or plant part is resistant to nematode infestation.

In another aspect, the invention provides a method of producing a soybean plant protected against nematode infestation, comprising transforming a soybean plant cell with a nucleic acid molecule encoding a Vip3 protein; and regenerating a transformed soybean plant from the soybean plant cell, wherein the transformed plant is protected against nematode infestation.

According to another aspect, the invention provides a method of producing a soybean plant protected against nematode infestation, comprising crossing a first parent soybean plant with a second parent soybean plant, wherein the first or second parent soybean plant comprises a heterologous nucleic acid molecule encoding a Vip3 protein, thereby producing a plurality of progeny plants; and selecting from the plurality of progeny plants, a transgenic plant that is protected against nematode infestation.

In another aspect of the invention, a method of reducing nematode cyst development on roots of a plant infectable by a nematode is provided, comprising introducing into cells of the root a nucleic acid molecule capable of directing the expression of a Vip3 protein, thereby reducing nematode cyst development on roots of the plant.

In another aspect, the invention provides a method of controlling or preventing nematode growth comprising providing a nematode pest with plant material comprising a heterologous DNA capable of directing expression of a Vip3 protein, wherein said plant inhibits a nematode biological activity.

In yet another aspect of the invention a method of providing a grower with a means of controlling nematode pests is provided, the method comprising supplying seed to a grower, wherein the seed comprises a heterologous nucleic acid molecule that encodes a Vip3 protein and wherein the seed is capable of producing a plant that is resistant to nematode infestation.

In another aspect of the invention, a method of suppressing growth of a plant-pathogenic nematode population in a location capable of supporting growth of the nematode population is provided comprising growing in the location a population of transgenic soybean plants comprising a heterologous nucleic acid molecule capable of directing expression of a Vip3 protein, wherein growth of the plant-pathogenic nematode population is suppressed.

The invention also provides a method of controlling *Heterodera glycines* comprising providing a transgenic soybean plant comprising an expression cassette having SEQ ID NO: 1 operably linked to a promoter capable of driving expression of an encoded Vip3 protein to levels sufficient to inhibit nematodes, wherein the proliferation of *Heterodera glycines* feeding on the soybean plant is reduced compared to *Heterodera glycines* feeding on a non-transgenic soybean plant not comprising the expression cassette.

According to another aspect, the invention provides a method of improving plant yield in nematode infested fields, comprising expressing in the plant a Vip3 protein, wherein plant yield is improved compared to yield of a plant of the same type not expressing a Vip3 protein.

In another aspect, the invention provides a method of increasing the vigor or yield in a transgenic soybean plant exposed to a population of nematodes comprising: introgressing a transgenic soybean event into a soybean plant resulting in a transgenic soybean plant, wherein the transgenic soybean event comprises a heterologous DNA sequence encoding a Vip3 protein that confers upon the transgenic soybean event resistance to nematodes; and growing the transgenic soybean plant or progeny thereof at a location where nematode infestation is yield limiting to a soybean plant not comprising the heterologous nucleic acid molecule encoding the Vip3 protein, whereby the transgenic soybean plant has increased vigor or yield compared to the control plant.

In another aspect, the invention provides a method of improving yield of a soybean field, comprising: introducing into a soybean plant a nucleic acid molecule capable of directing expression of a Vip3 protein, thus producing a transgenic plant; and cultivating a plurality of transgenic seeds from the transgenic plant in a filed producing a, resulting in a soybean field comprising a plurality of transgenic soybean plants having enhanced resistance to nematode infestation, thereby improving yield of the soybean field.

The present invention also provides a recombinant expression cassette comprising a heterologous promoter sequence operatively linked to a nucleic acid molecule encoding a Vip3 protein. Further, the present invention provides a recombinant vector comprising such an expression cassette. Still further, the present invention provides a transgenic host cell comprising such an expression cassette. A transgenic host cell according to this aspect of the invention may be a plant cell. Even further, the present invention provides a transgenic plant or plant part comprising such a plant cell.

The present invention also provides a nematicidal composition comprising an effective nematode-controlling amount of a Vip3 protein and an acceptable agricultural carrier. In another aspect, the agricultural carrier is a transgenic plant. In yet another aspect, the transgenic plant is a transgenic soybean plant and the Vip3 protein is a Vip3A protein having at least 82% sequence identity with SEQ ID NO: 1. In another aspect, the Vip3A protein comprises SEQ ID NO: 1.

In a further aspect, the present invention provides a method of producing a nematode-resistant transgenic plant, comprising introducing a nucleic acid molecule encoding a Vip3 protein into a plant cell thereby making a transgenic plant cell; regenerating a transgenic plant from the transgenic plant cell, wherein the Vip3A protein is expressible in the transgenic plant in an effective amount to control nematodes. According to another aspect, the plant is a soybean plant. In another aspect, the Vip3 protein is a Vip3A protein having at least 82% sequence identity with SEQ ID NO: 1. In yet another aspect, the Vip3A protein comprises SEQ ID NO: 1. In still another aspect, the nematode is a cyst forming nematode. In another aspect, the cyst forming nematode is is the genus *Heterodera*. In still another aspect the cyst nematode is soybean cyst nematode (*Heterodera glycines*).

Other aspects and advantages of the invention will become apparent to those skilled in the art from a study of the following description of the invention and non-limiting examples.

BRIEF DESCRIPTION OF THE SEQUENCES IN THE SEQUENCE LISTING

SEQ ID NO: 1 is an amino acid sequence of a Vip3Aa20 protein.
SEQ ID NO: 2 is a nucleotide sequence encoding SEQ ID NO: 1.

SEQ ID NO: 3 is an amino acid sequence of a Vip3Aa1 protein.
SEQ ID NO: 4 is a nucleotide sequence encoding SEQ ID NO: 3.
SEQ ID NO: 5 is a nucleotide sequence encoding SEQ ID NO: 3.
SEQ ID NO: 6 is an amino acid sequence of a Vip3Aa2 protein.
SEQ ID NO: 7 is a nucleotide sequence encoding SEQ ID NO: 6.
SEQ ID NO: 8 is an amino acid sequence of a Vip3Aa3 protein.
SEQ ID NO: 9 is a nucleotide sequence encoding SEQ ID NO: 8.
SEQ ID NO: 10 is an amino acid sequence of a Vip3Af2 protein.
SEQ ID NO: 11 is a nucleotide sequence encoding SEQ ID NO: 10.
SEQ ID NO: 12 is an amino acid sequence of a Vip3Af4 protein.
SEQ ID NO: 13 is a nucleotide sequence encoding SEQ ID NO: 12.
SEQ ID NO: 14 is an amino acid sequence of a Vip3Af5 protein.
SEQ ID NO: 15 is a nucleotide sequence encoding SEQ ID NO: 14.
SEQ ID NO: 16 is an amino acid sequence of a Vip3Ag1 protein.
SEQ ID NO: 17 is a nucleotide sequence encoding SEQ ID NO: 16.
SEQ ID NO: 18 is the nucleotide sequence of the vector pKS214.
SEQ ID NO: 19 is a Vip3-identifying amino acid sequence.

DETAILED DESCRIPTION

Before explaining the various embodiments of the disclosure, it is to be understood that the invention is not limited in its application to the details of construction and the arrangement of the components set forth in the following description. Other embodiments can be practiced or carried out in various ways. Also, it is to be understood that the phraseology and terminology employed herein is for the purpose of description and should not be regarded as limiting.

Throughout this disclosure, various publications, patents and published patent specifications are referenced. Where permissible, the disclosures of these publications, patents and published patent specifications are hereby incorporated by reference in their entirety into the present disclosure to more fully describe the state of the art. Unless otherwise indicated, the disclosure encompasses conventional techniques of plant breeding, immunology, molecular biology, microbiology, cell biology and recombinant DNA, which are within the skill of the art. See, e.g., Sambrook and Russell, Molecular Cloning: A Laboratory Manual, 3rd edition (2001); Current Protocols in Molecular Biology [(F. M. Ausubel, et al. eds., (1987)]; Plant Breeding: Principles and Prospects (Plant Breeding, Vol 1) M. D. Hayward, N, O. Bosemark, I. Romagosa; Chapman & Hall, (1993.); Coligan, Dunn, Ploegh, Speicher and Wingfeld, eds. (1995) CURRENT Protocols in Protein Science (John Wiley & Sons, Inc.); the series Methods in Enzymology (Academic Press, Inc.): PCR 2: A Practical Approach (M. J. MacPherson, B. D. Flames and G. R. Taylor eds. (1995)], Harlow and Lane, eds. (1988) Antibodies, A Laboratory Manual, and Animal Cell Culture [R. I. Freshney, ed. (1987)].

Unless otherwise noted, technical terms are used according to conventional usage. Definitions of common terms in molecular biology may be found in Lewin, Genes VII, published by Oxford University Press, 2000; Kendrew et al. (eds.), The Encyclopedia of Molecular Biology, published by Wiley-Interscience, 1999; and Robert A. Meyers (ed.), Molecular Biology and Biotechnology, a Comprehensive Desk Reference, published by VCH Publishers, Inc., 1995; Ausubel et al. (1987) Current Protocols in Molecular Biology, Green Publishing; Sambrook and Russell. (2001) Molecular Cloning: A Laboratory Manual 3rd. edition.

In order to facilitate understanding of the disclosure, the following definitions are provided:

"Activity" of the Vip3 proteins of the invention is meant that the Vip3 proteins have a toxic effect on nematodes by disrupting or detering feeding, inhibiting the ability of nematode pests to survive, grow and reproduce which may or may not cause death of the nematode, or of limiting nematode-related damage or loss to crop plants.

As used herein, "and/or" refers to and encompasses any and all possible combinations of one or more of the associated listed items, as well as lack of combinations when interpreted in the alternative (or).

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

As used herein, the term "contacting" refers to a process by which a Vip3 protein of the invention or transgenic plant or plant part expressing the Vip3 protein of the invention are delivered or administered to target nematode pests or nematode pest populations. Contacting describes physical proximity of Vip3 proteins or transgenic plants or plant parts expressing a Vip3 protein and the target nematode so that they interact. The transgenic plants or plant parts may be contacted with a target nematode or nematode population by planting transgenic seed, transgenic seedlings, cuttings, plant runners, tubers, and the like in a location capable of supporting growth of a nematode pest or nematode pest population.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein the terms "to control" or "controlling" nemtodes means to inhibit, through a toxic effect, the ability of nemtode pests to survive, grow, feed, and/or reproduce, or to limit nematode-related damage or loss in crop plants. To "control" nematodes may or may not mean killing the nemtodes.

Corresponding to: in the context of the present invention, "corresponding to" or "corresponds to" means that when the nucleic acid coding sequences or amino acid sequences of different Vip3 genes or proteins are aligned with each other, the nucleic or amino acids that "correspond to" certain enumerated positions are those that align with these positions but that are not necessarily in these exact numerical positions relative to the particular Vip3's respective nucleic acid coding sequence or amino acid sequence. Likewise, when the coding or amino acid sequence of a particular Vip3 (for example, Vip3Ag1) is aligned with the coding or amino acid sequence of a reference Vip3 (for example, Vip3Aa20), the nucleic acids or amino acids in the Vip3Ag1 sequence that "correspond to" certain enumerated positions of the Vip3Aa20 sequence are those that align with these positions of the Vip3Aa20 sequence, but are not necessarily in these exact numerical positions of the Vip3Ag1protein's respective nucleic acid coding sequence or amino acid sequence.

To "deliver" a toxin means that the toxin comes in contact with a nematode or nematode population, resulting in a toxic effect and control of the nematode or nematode population. The toxin can be delivered in many recognized ways, e.g., orally by ingestion by the nematode or by contact with the nematode via transgenic plant expression, formulated protein composition(s), sprayable protein composition(s), a bait matrix, or any other art-recognized toxin delivery system.

The term "economic threshold" is defined as the pest nematode population that produces incremental damage equal to the cost of controlling or preventing that damage. It is the level of nematode population where the benefit of nematode control is equal to its cost. In this regard, economic threshold may be defined as the nematode pest damage level where the value of incremental reduction in crop yield is equal to the cost of preventing its occurrence. In other words, economic threshold attempts to determine the point at which it becomes economically feasible to control a nematode pest population. Economic damage to the host crop normally is inflicted by the first generation progeny of nematodes and is prevented by transgenic plants expressing a Vip3 protein through lowering the concentration of progeny nematodes in the plant root zone.

A "nematode-controlling effective amount" as used herein refers to the concentration of a Vip3 toxin capable of inhibiting, through a toxic effect, the ability of nematodes to survive, grow, feed and/or reproduce, or of reducing or preventing nematode-related damage or loss in crop plants. "Nematode-controlling effective amount" may or may not mean killing the nematodes.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

A "heterologous" nucleic acid sequence is a nucleic acid sequence not naturally associated with a host cell into which it is introduced, including non-naturally occurring multiple copies of a naturally occurring nucleic acid sequence.

"Nematicidal" is defined as a toxic biological activity capable of controlling nematodes, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence. For example, a native coding sequence from Bacillus spp. that encodes a Vip3 protein is isocoding with a coding sequence codon optimized for expression in a plant that encodes the same Vip3 protein.

An "isolated" nucleic acid molecule or an isolated protein or toxin is a nucleic acid molecule or protein or toxin that, by the hand of man, exists apart from its native environment and is therefore not a product of nature. An isolated nucleic acid molecule or protein or toxin may exist in a purified form or may exist in a non-native environment such as, for example, a recombinant host cell or a transgenic plant.

The term "native" refers to a coding sequence or gene that is naturally present in the genome of a cell or plant.

The term "naturally occurring" is used herein to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of higher organized unit such as, for example, plant tissue, a plant organ, or a whole plant.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

A "plant part" may be any part of a plant and include a plant cell, plant material, plant organ or plant tissue.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase II and initiates transcription of the DNA. The promoter region may also include other elements that act as regulators of gene expression.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

As used herein, "resistant" or resistance means a transgenic soybean variety that prevents a majority of nematodes from surviving and/or reproducing upon their attempted infestation.

The term "substantially identical," in the context of two nucleic acid or protein sequences, refers to two or more sequences or subsequences that have at least 60%, preferably 80%, more preferably 90, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In an especially preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic* Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook, et al., In: Molecular Cloning A Laboratory Manual, 2nd Edition, Cold Spring Harbor Press, Cold Spring Harbor, N.Y. (1989), and by Haymes, et al. In: Nucleic Acid Hybridization, A Practical Approach, IRL Press, Washington, D.C. (1985), herein incorporated by reference in its entirety.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference vip3 nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Synthetic" refers to a nucleotide sequence comprising structural characters that are not present in the natural sequence. For example, a vip3 coding sequence, naturally found in Bacillus, that resembles more closely the G+C content and the normal codon distribution of dicot and/or monocot genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

A "Vip3 protein" in the context of the invention means a vegetative insecticidal protein (VIP) that is a member of the Vip3 class including for example without limitation, Vip3Aa1, Vip3Aa2, Vip3Aa3, Vip3Aa19, Vip3Aa20, Vip3Af2, Vip3Ag1, and their homologues. Some structural features that identify a protein as being in the Vip3 class of proteins includes, 1) a size of about 80 kDa; and 2) a highly conserved N-terminal secretion signal that comprises the amino acid sequence IYGFATGIKDI (SEQ ID NO: 19) which is not processed during secretion in Bacillus. A nematode-active "homologue" as used herein means that the indicated protein or polypeptide is active against nematodes and bears a defined relationship to other members of the Vip3 class of proteins. This defined relationship may include but is not limited to, 1) proteins which are at least 70%, or least 80%, or at least 90% identical at the sequence level to another member of the Vip3 class of proteins while also retaining nematicidal activity, 2) proteins which are cross-reactive to antibodies which immunologically recognize another member of the Vip3 class of proteins, 3) proteins which are cross-reactive with a nematode receptor to another member of the Vip3 class of proteins and retain nematode activity when expressed in a transgenic plant, and 4) proteins which are at least 70%, or at least 80%, or at least 90% identical at the sequence level to a toxic core region of another member of the Vip3 class of proteins while also retaining nematicidal activity. Non-limiting examples of members of the Vip3 class including those previously mentioned and their respective GenBank accession numbers or US Patent or patent publication number are Vip3Aa1 (AAC37036), Vip3Aa2 (AAC37037), Vip3Aa3 (U.S. Pat. No. 6,137,033), Vip3Aa4 (AAR81079), Vip3Aa5 (AAR81080), Vip3Aa6 (AAR81081), Vip3Aa7 (AAK95326), Vip3Aa8 (AAK97481), Vip3Aa9 (CAA76665), Vip3Aa10 (AAN60738), Vip3Aa11

(AAR36859), Vip3Aa12 (AAM22456), Vip3Aa13 (AAL69542), Vip3Aa14 (AAQ12340), Vip3Aa15 (AAP51131), Vip3Aa16 (AAW65132), Vip3Aa17 (U.S. Pat. No. 6,603,063), Vip3Aa18 (AAX49395), Vip3Aa19 (DQ241674), Vip3Aa19(DQ539887), Vip3Aa20 (DQ539888), Vip3Aa21 (ABD84410), Vip3Aa22 (AAY41427), Vip3Aa23 (AAY41428), Vip3Aa24 (BI 880913), Vip3Aa25 (EF608501), Vip3Aa26(EU294496), Vip3Aa27 (EU332167), Vip3Aa28 (FJ494817), Vip3Aa29 (FJ626674), Vip3Aa30 (FJ626675), Vip3Aa31 (FJ626676), Vip3Aa32(FJ626677), Vip3Aa33(GU073128), Vip3Aa34 (GU073129), Vip3Aa35 (GU733921), Vip3Aa36 (GU951510), Vip3Aa37 (HM132041), Vip3Aa38 (HM117632), Vip3Aa39 (HM117631), Vip3Aa40 (HM132042), Vip3Aa41 (HM132043), Vip3Aa42 (HQ587048), Vip3Aa43 (HQ594534), Vip3Aa44 (HQ650163), Vip3Ab1 (AAR40284), Vip3Ab2 (AAY88247), Vip3Ac1 (US Patent Application Publication 20040128716), Vip3Ad1 (US Patent Application Publication 20040128716), Vip3Ad2 (CAI43276), Vip3Ae1 (CAI43277), Vip3Af1 (CAI43275), Vip3Af2 (ADN08753), Vip3Af3 (HM117634), Vip3Ag1 (ADN08758), Vip3Ag2 (FJ556803), Vip3Ag3 (HM117633), Vip3Ag4 (HQ414237), Vip3Ag5 (HQ542193), and Vip3Ah1 (DQ832323).

As used herein, nucleotides are indicated by their bases by the following standard abbreviations: adenine (A), cytosine (C), thymine (T), and guanine (G) Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The materials and methods of the subject invention are useful for killing or controlling nematodes; retarding growth or reproduction of nematodes; reducing nematode populations; and/or reducing or retarding damage to plants caused by infestation of nematode pests. In particular, the invention provides methods of controlling nematode pests of crop plants such as soybean by using transgenic crop plants expressing a Vip3 protein.

The expression in transgenic plants or plant parts of the Vip3 proteins of the invention results in compositions that can be used to control nematode pests, for example, without limitation, *Meloidogyne* spp. (for example, *Meloidogyne incoginita* and *Meloidogyne javanica, Meloidogyne hapla, Meloidogyne arenari*), *Heterodera* spp. (for example, *Heterodera glycines, Heterodera carotae, Heterodera schachtii, Heterodora avenae* and *Heterodora trifolii*), *Globodera* spp. (for example, *Globodera rostochiensis*), *Radopholus* spp. (for example, *Radopholus similes*), *Rotylenchulus* spp., *Pratylenchus* spp. (for example, *Pratylenchus neglectans* and *Pratylenchus penetrans*), *Aphelenchoides* spp., *Helicotylenchus* spp., *Hoplolaimus* spp., *Paratrichodorus* spp., *Longidorus* spp., *Nacobbus* spp., *Subanguina* spp. *Belonlaimus* spp., *Criconemella* spp., *Criconemoides* spp. *Ditylenchus* spp., *Ditylenchus dipsaci, Dolichodorus* spp., *Hemicriconemoides* spp., *Hemicycliophora* spp., *Hirschmaniella* spp., *Hypsoperine* spp., *Macroposthonia* spp., *Melinius* spp., *Punctodera* spp., *Quinisulcius* spp., *Scutellonema* spp., *Xiphinema* spp., and *Tylenchorhynchus* spp.

In one embodiment, the invention encompasses a method of controlling a nematode pest, comprising contacting the nematode pest with a Vip3 protein comprising SEQ ID NO: 19.

In another embodiment, the nematode is selected from the group consisting of *Criconemella, Ditylenchus, Globodera, Helicotylenchus, Heterodera, Longidorus, Meloidogyne, Paratrichodorus, Pratylenchus, Radopholus, Rotelynchus, Rotylenchulus, Tylenchulus* and *Xiphinema*. In yet another embodiment, the nematode is a cyst forming nematode. In still another embodiment, the nematode is in the genus *Heterodera*. In a further embodiment, the nematode is *Heterodera glycines*.

In another embodiment, the contacting step is carried out with a plant or plant part transformed with at least one nucleic acid molecule encoding the Vip3 protein. In yet another embodiment, the plant or plant part is a soybean plant or plant part. In still another embodiment, the soybean plant part is a soybean root.

In another embodiment, the Vip3 protein is a Vip3A protein. In yet another embodiment, the Vip3A protein comprises an amino acid sequence that is the translation product of a nucleotide sequence whose complement hybridizes to SEQ ID NO: 2, SEQ ID NO: 4, SEQ ID NO: 5, SEQ ID NO: 7, SEQ ID NO: 9, SEQ ID NO: 11, SEQ ID NO: 13, SEQ ID NO: 15 or SEQ ID NO: 17 under high-stringency conditions. In still another embodiment, the high-stringency conditions are 7% sodium dodecyl sulfate (SDS), 0.5 M NaP$_{O4}$, 1 mM EDTA at 50° C. with washing in 0.1×SSC, 0.1% SDS at 65° C. In a further embodiment, the Vip3A protein is selected from the group consisting of Vip3Aa1 (AAC37036), Vip3Aa2 (AAC37037), Vip3Aa3 (U.S. Pat. No. 6,137,033), Vip3Aa4 (AAR81079), Vip3Aa5 (AAR81080), Vip3Aa6 (AAR81081), Vip3Aa7 (AAK95326), Vip3Aa8 (AAK97481), Vip3Aa9 (CAA76665), Vip3Aa10 (AAN60738), Vip3Aa11 (AAR36859), Vip3Aa12 (AAM22456), Vip3Aa13 (AAL69542), Vip3Aa14 (AAQ12340), Vip3Aa15 (AAP51131), Vip3Aa16 (AAW65132), Vip3Aa17 (U.S. Pat. No. 6,603,063), Vip3Aa18 (AAX49395), Vip3Aa19 (DQ241674), Vip3Aa19 (DQ539887), Vip3Aa20 (DQ539888), Vip3Aa21 (ABD84410), Vip3Aa22 (AAY41427), Vip3Aa23 (AAY41428), Vip3Aa24 (BI 880913), Vip3Aa25 (EF608501), Vip3Aa26 (EU294496), Vip3Aa27 (EU332167), Vip3Aa28 (FJ494817), Vip3Aa29 (FJ626674), Vip3Aa30 (FJ626675), Vip3Aa31 (FJ626676), Vip3Aa32 (FJ626677), Vip3Aa33 (GU073128), Vip3Aa34 (GU073129), Vip3Aa35 (GU733921), Vip3Aa36 (GU951510), Vip3Aa37 (HM132041), Vip3Aa38 (HM117632), Vip3Aa39 (HM117631), Vip3Aa40 (HM132042), Vip3Aa41 (HM132043), Vip3Aa42 (HQ587048), Vip3Aa43 (HQ594534), Vip3Aa44 (HQ650163), Vip3Ab1 (AAR40284), Vip3Ab2 (AAY88247), Vip3Ac1 (US Patent Application Publication 20040128716), Vip3Ad1 (US Patent Application Publication 20040128716), Vip3Ad2 (CAI43276), Vip3Ae1 (CAI43277), Vip3Af1 (CAI43275), Vip3Af2 (ADN08753), Vip3Af3 (HM117634), Vip3Ag1 (ADN08758), Vip3Ag2 (FJ556803), Vip3Ag3 (HM117633), Vip3Ag4 (HQ414237), Vip3Ag5 (HQ542193), and Vip3Ah1 (DQ832323). In yet another embodiment, the Vip3A protein comprises SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16, or a nematode-active homologue thereof having at least 80%, 81%, 82%, 83%, 84%, 85%, 86%, 87%, 88%, 89%, 90%, 91%, 92%, 93%, 94%, 95%, 96%, 97%, 98% or 99% identity with SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16. In another embodiment, the Vip3A protein comprises SEQ ID NO: 1 or a nematode-active homologue having at least 80%, 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1.

In one embodiment, the invention encompasses a plant or plant part infestable by a nematode and which is protected from the nematode by being transformed with at least one nucleic acid molecule encoding a Vip3 protein. In another embodiment, the plant or plant part is a soybean plant or plant part. In another embodiment, the nematode is in the genus *Heterodera*. In still another embodiment, the nematode is *Heterodera glycines*.

In one embodiment, the invention encompasses a method of controlling a nematode pest, comprising contacting the nematode pest with a transgenic plant or plant part comprising a heterologous nucleic acid molecule that directs expression of a Vip3 protein in the transgenic plant, wherein the transgenic plant controls the nematode pest compared to a plant of the same type that does not express the Vip3 protein.

In another embodiment, the nematode is selected from the group consisting of *Criconemella, Ditylenchus, Globodera, Helicotylenchus, Heterodera, Longidorus, Meloidogyne, Paratrichodorus, Pratylenchus, Radolpholus, Rotelynchus, Rotylenchulus, Tylenchulus* and *Xiphinema*. In yet another embodiment, the nematode is a cyst forming nematode. In still another embodiment, the nematode is in the genus *Heterodera*. In a further embodiment, the nematode is *Heterodera glycines*.

In another embodiment, the transgenic plant or plant part is selected from the group consisting of alfalfa, apple, apricot, *Arabidopsis*, artichoke, asparagus, avocado, banana, barley, beans, beet, blackberry, blueberry, *Brassica*, broccoli, Brussels sprouts, cabbage, canola, carrot, cassava, cauliflower, a cereal, celery, cherry, citrus, Clementine, coffee, corn, cotton, cucumber, eggplant, endive, eucalyptus, figs, grape, grapefruit, groundnuts, ground cherry, kiwifruit, lettuce, leek, lemon, lime, pine, maize, mango, melon, millet, mushroom, nut oat, okra, onion, orange, an ornamental plant or flower or tree, papaya, parsley, pea, peach, peanut, peat, pepper, persimmon, pineapple, plantain, plum, pomegranate, potato, pumpkin, radicchio, radish, rapeseed, raspberry, rice, rye, sorghum, soy, soybean, spinach, strawberry, sugar beet, sugarcane, sunflower, sweet potato, tangerine, tea, tobacco, tomato, a vine, watermelon, wheat, yams and zucchini. In yet another embodiment, the transgenic plant or plant part is a soybean plant or plant part.

In another embodiment, the Vip3 protein is a Vip3A protein. In yet another embodiment, the Vip3A protein comprises an amino acid sequence that is the translation product of a nucleotide sequence whose complement hybridizes to SEQ ID NO: 2, SEQ ID NO: 4, SEQ ID NO: 5, SEQ ID NO: 7, SEQ ID NO: 9, SEQ ID NO: 11, SEQ ID NO: 13, SEQ ID NO: 15 or SEQ ID NO: 17 under high-stringency conditions. In still another embodiment, the high-stringency conditions are 7% sodium dodecyl sulfate (SDS), 0.5 M NaP$_{O4}$, 1 mM EDTA at 50° C. with washing in 0.1×SSC, 0.1% SDS at 65° C. In a further embodiment, the Vip3A protein is selected from the group consisting of Vip3Aa1 (AAC37036), Vip3Aa2 (AAC37037), Vip3Aa3 (U.S. Pat. No. 6,137,033), Vip3Aa4 (AAR81079), Vip3Aa5 (AAR81080), Vip3Aa6 (AAR81081), Vip3Aa7 (AAK95326), Vip3Aa8 (AAK97481), Vip3Aa9 (CAA76665), Vip3Aa10 (AAN60738), Vip3Aa11 (AAR36859), Vip3Aa12 (AAM22456), Vip3Aa13 (AAL69542), Vip3Aa14 (AAQ12340), Vip3Aa15 (AAP51131), Vip3Aa16 (AAW65132), Vip3Aa17 (U.S. Pat. No. 6,603,063), Vip3Aa18 (AAX49395), Vip3Aa19 (DQ241674), Vip3Aa19 (DQ539887), Vip3Aa20 (DQ539888), Vip3Aa21 (ABD84410), Vip3Aa22 (AAY41427), Vip3Aa23 (AAY41428), Vip3Aa24 (BI 880913), Vip3Aa25 (EF608501), Vip3Aa26 (EU294496), Vip3Aa27 (EU332167), Vip3Aa28 (FJ494817), Vip3Aa29 (FJ626674), Vip3Aa30 (FJ626675), Vip3Aa31 (FJ626676), Vip3Aa32 (FJ626677), Vip3Aa33 (GU073128), Vip3Aa34 (GU073129), Vip3Aa35 (GU733921), Vip3Aa36 (GU951510), Vip3Aa37 (HM132041), Vip3Aa38 (HM117632), Vip3Aa39 (HM117631), Vip3Aa40 (HM132042), Vip3Aa41 (HM132043), Vip3Aa42 (HQ587048), Vip3Aa43 (HQ594534), Vip3Aa44 (HQ650163), Vip3Ab1 (AAR40284), Vip3Ab2 (AAY88247), Vip3Ac1 (U.S. Pat. Application Publication 20040128716), Vip3Ad1 (US Patent Application Publication 20040128716), Vip3Ad2 (CAI43276), Vip3Ae1 (CAI43277), Vip3Af1 (CAI43275), Vip3Af2 (ADN08753), Vip3Af3 (HM117634), Vip3Ag1 (ADN08758), Vip3Ag2 (FJ556803), Vip3Ag3 (HM117633), Vip3Ag4 (HQ414237), Vip3Ag5 (HQ542193), and Vip3Ah1 (DQ832323). In still a further embodiment, the Vip3A protein comprises SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16, or a nematode-active homologue thereof having at least 80%, 81%, 82%, 83%, 84%, 85%, 86%, 87%, 88%, 89%, 90%, 91%, 92%, 93%, 94%, 95%, 96%, 97%, 98% or 99% identity with SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16. In another embodiment, the Vip3A protein comprises SEQ ID NO: 1 or a nematode-active homologue having at least 80%, 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1.

In another embodiment, the transgenic plant further comprises or expresses at least one additional pesticidal agent selected from the group consisting of a patatin, a *Bacillus thuringiensis* insecticidal protein, a *Bacillus thuringiensis* nematicidal protein, a *Xenorhabdus* insecticidal protein, a *Photorhabdus* insecticidal protein, a *Bacillus laterosporous* insecticidal protein, and a *Bacillus sphearicus* insecticidal protein. In yet another embodiment, the *Bacillus thuringiensis* nematicidal protein is selected from the group consisting of a Cry1, Cry3, Cry11, Cry12, Cry13, Cry14, Cry21, and Cry22.

In one embodiment, the invention encompasses a method of conferring nematode resistance to a plant or plant part comprising inserting into the plant or plant part a heterologous nucleic acid molecule encoding a Vip3 protein, wherein the plant or plant part expresses the Vip3 protein at a nematode-inhibiting level so as to confer nematode resistance to the plant or plant part compared to the same type of plant or plant part not expressing the Vip3 protein.

In another embodiment, the nematode is selected from the group consisting of *Criconemella, Ditylenchus, Globodera, Helicotylenchus, Heterodera, Longidorus, Meloidogyne, Paratrichodorus, Pratylenchus, Radolpholus, Rotelynchus, Rotylenchulus, Tylenchulus* and *Xiphinema*. In yet another embodiment, the nematode is a cyst forming nematode. In still another embodiment, the nematode is in the genus *Heterodera*. In a further embodiment, the nematode is *Heterodera glycines*.

In another embodiment, the plant or plant part is selected from the group consisting of alfalfa, apple, apricot, *Arabidopsis*, artichoke, asparagus, avocado, banana, barley, beans, beet, blackberry, blueberry, *Brassica*, broccoli, Brussels sprouts, cabbage, canola, carrot, cassava, cauliflower, a cereal, celery, cherry, citrus, Clementine, coffee, corn, cotton, cucumber, eggplant, endive, eucalyptus, figs, grape, grapefruit, groundnuts, ground cherry, kiwifruit, lettuce, leek, lemon, lime, pine, maize, mango, melon, millet, mushroom, nut oat, okra, onion, orange, an ornamental plant or flower or tree, papaya, parsley, pea, peach, peanut, peat, pepper, persimmon, pineapple, plantain, plum, pomegranate, potato, pumpkin, radicchio, radish, rapeseed, raspberry, rice, rye, sorghum, soy, soybean, spinach, strawberry, sugar beet, sugarcane, sunflower, sweet potato, tangerine, tea, tobacco, tomato, a vine, watermelon, wheat, yams and zucchini. In yet another embodiment, the plant or plant part is a soybean plant or plant part.

In another embodiment, the Vip3 protein is a Vip3A protein. In yet another embodiment, the Vip3A protein comprises an amino acid sequence that is the translation product of a nucleotide sequence whose complement hybridizes to SEQ ID NO: 2, SEQ ID NO: 4, SEQ ID NO: 5, SEQ ID NO: 7, SEQ ID NO: 9, SEQ ID NO: 11, SEQ ID NO: 13, SEQ ID NO: 15 or SEQ ID NO: 17 under high-stringency conditions. In still another embodiment, the high-stringency conditions are 7% sodium dodecyl sulfate (SDS), 0.5 M NaP$_{O4}$, 1 mM EDTA at 50° C. with washing in 0.1×SSC, 0.1% SDS at 65° C. In a further embodiment, the Vip3A protein is selected from the group consisting of Vip3Aa1 (AAC37036), Vip3Aa2 (AAC37037), Vip3Aa3 (U.S. Pat. No. 6,137,033), Vip3Aa4 (AAR81079), Vip3Aa5 (AAR81080), Vip3Aa6 (AAR81081), Vip3Aa7 (AAK95326), Vip3Aa8 (AAK97481), Vip3Aa9 (CAA76665), Vip3Aa10 (AAN60738), Vip3Aa11 (AAR36859), Vip3Aa12 (AAM22456), Vip3Aa13 (AAL69542), Vip3Aa14 (AAQ12340), Vip3Aa15 (AAP51131), Vip3Aa16 (AAW65132), Vip3Aa17 (U.S. Pat. No. 6,603,063), Vip3Aa18 (AAX49395), Vip3Aa19 (DQ241674), Vip3Aa19 (DQ539887), Vip3Aa20 (DQ539888), Vip3Aa21 (ABD84410), Vip3Aa22 (AAY41427), Vip3Aa23 (AAY41428), Vip3Aa24 (BI 880913), Vip3Aa25 (EF608501), Vip3Aa26 (EU294496), Vip3Aa27 (EU332167), Vip3Aa28 (FJ494817), Vip3Aa29 (FJ626674), Vip3Aa30 (FJ626675), Vip3Aa31 (FJ626676), Vip3Aa32 (FJ626677), Vip3Aa33 (GU073128), Vip3Aa34 (GU073129), Vip3Aa35 (GU733921), Vip3Aa36 (GU951510), Vip3Aa37 (HM132041), Vip3Aa38 (HM117632), Vip3Aa39 (HM117631), Vip3Aa40 (HM132042), Vip3Aa41 (HM132043), Vip3Aa42 (HQ587048), Vip3Aa43 (HQ594534), Vip3Aa44 (HQ650163), Vip3Ab1 (AAR40284), Vip3Ab2 (AAY88247), Vip3Ac1 (US Patent Application Publication 20040128716), Vip3Ad1 (US Patent Application Publication 20040128716), Vip3Ad2 (CAI43276), Vip3Ae1 (CAI43277), Vip3Af1 (CAI43275), Vip3Af2 (ADN08753), Vip3Af3 (HM117634), Vip3Ag1 (ADN08758), Vip3Ag2 (FJ556803), Vip3Ag3 (HM117633), Vip3Ag4 (HQ414237), Vip3Ag5 (HQ542193), and Vip3Ah1 (DQ832323). In still a further embodiment, the Vip3A protein comprises SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16, or a nematode-active homologue thereof having at least 80%, 81%, 82%, 83%, 84%, 85%, 86%, 87%, 88%, 89%, 90%, 91%, 92%, 93%, 94%, 95%, 96%, 97%, 98% or 99% identity with SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16. In another embodiment, the Vip3A protein comprises SEQ ID NO: 1 or a nematode-active homologue having at least 80%, 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1.

In another embodiment, transgenic plant or plant part further comprises or expresses at least one additional pesticidal agent selected from the group consisting of a patatin, a *Bacillus thuringiensis* insecticidal protein, a *Bacillus thuringiensis* nematicidal protein, a *Xenorhabdus* insecticidal protein, a *Photorhabdus* insecticidal protein, a *Bacillus laterosporous* insecticidal protein, and a *Bacillus sphearicus* insecticidal protein. In yet another embodiment, the *Bacillus thuringiensis* nematicidal protein is selected from the group consisting of a Cry1, Cry3, Cry11, Cry12, Cry13, Cry14, Cry21, and Cry22.

In one embodiment, the invention encompasses a method of reducing nematode infectivity to a plant comprising contacting the nematode with a Vip3 protein, wherein nematode infectivity is reduced compared to nematode infectivity of plant not contacted with a Vip3 protein. In another embodiment, the contacting step comprises planting a transgenic seed capable of producing a transgenic plant that expresses a Vip3 protein, wherein the nematode feeds on the transgenic plant. In yet another embodiment, the transgenic plant is soybean (*Glycine max*). In still another embodiment, the nematode is soybean cyst nematode (*Heterodera glycines*).

In one embodiment, the invention encompasses method of improving plant yield in nematode infested fields, comprising expressing in the plant a Vip3 protein, wherein plant yield is improved compared to yield of a plant of the same type not expressing a Vip3 protein.

In another embodiment, the invention encompasses a method of producing a soybean plant protected against nematode infestation comprising transforming a soybean plant cell with a nucleic acid molecule encoding a Vip3 protein and regenerating a transformed soybean plant from the soybean plant cell.

In another embodiment, the invention encompasses a method of producing a soybean plant protected against nematode infestation comprising crossing a first parent soybean plant with a second parent soybean plant, wherein said first or second parent soybean plant comprises a heterologous nucleic acid molecule encoding a Vip3 protein, thereby producing a plurality of progeny plants; and selecting from the plurality of progeny plants, a transgenic plant that is protected against nematode infestation.

In still another embodiment, the invention encompasses a method of providing a grower with a means of controlling nematode pests comprising supplying seed to a grower, wherein the seed comprises a heterologous nucleic acid molecule that encodes a Vip3 protein and wherein the seed is capable of producing a plant that is resistant to nematode damage.

In one embodiment, the invention encompasses a transgenic soybean plant or plant part comprising a heterologous nucleic acid molecule encoding a Vip3 protein, wherein said transgenic plant or plant part has improved resistance to at least one plant pathogenic nematode, as compared to a control plant or plant part not expressing the Vip3 protein. In another embodiment, the Vip3 protein comprises SEQ ID NO: 19. In still another embodiment, the Vip3 protein is a Vip3A protein. In a further embodiment, the Vip3A protein having at least 80%, 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1. In yet another embodiment, the Vip3A protein comprises SEQ ID NO: 1. In another embodiment, the cyst forking nematode is a soybean cyst nematode (*Heterodera glycines*).

In another embodiment, the invention encompasses transgenic seed of a transgenic plant of the invention, wherein the transgenic seed comprises a heterologous nucleic acid molecule encoding a Vip3 protein of the invention.

In yet another embodiment, the invention encompasses a method of controlling *Heterodera glycines* comprising providing a transgenic soybean plant or plant part comprising an expression cassette having SEQ ID NO: 2 operably linked to a promoter capable of driving expression of an encoded Vip3 protein to levels sufficient to inhibit nematodes, wherein the proliferation of *Heterodera glycines* cysts on said plant or plant part is reduced compared to *Heterodera glycines* cysts on a soybean plant or plant part not expressing the Vip3 protein. In another embodiment, the promoter is selected from the group consisting of: a) a constitutive promoter; b) a tissue-specific promoter; and c) an inducible promoter. In yet another embodiment, the promoter is an actin2 promoter.

In one embodiment, the invention encompasses a method of increasing the vigor or yield in a transgenic soybean plant exposed to a population of nematodes comprising introgressing a soybean event into a soybean plant resulting in a transgenic soybean plant, wherein the transgenic soybean event comprises a heterologous nucleic acid molecule encoding a Vip3 protein that confers upon the transgenic soybean event resistance to nematodes; and growing the transgenic soybean plant or progeny thereof at a location where nematode infestation is yield limiting to a soybean plant not comprising the heterologous nucleic acid molecule encoding the Vip3 protein, whereby the transgenic soybean plant has increased vigor or yield compared to the control plant.

The invention also encompasses a method of improving soybean yield comprising introducing into a soybean plant a nucleic acid molecule capable of directing expression of a Vip3 protein; and cultivating a plurality of transgenic seeds from the plant of step (a), resulting in a plurality of transgenic plants having enhanced resistance to nematode infestation, thereby improving soybean yield.

The invention further encompasses a nematicidal composition comprising a Vip3 protein and an acceptable agricultural carrier.

In another embodiment, the Vip3 protein comprises SEQ ID NO: 19. In still another embodiment the Vip3 protein is a Vip3A protein. In yet another embodiment, the Vip3A protein comprises an amino acid sequence that is the translation product of a nucleotide sequence whose complement hybridizes to SEQ ID NO: 2, SEQ ID NO: 4, SEQ ID NO: 5, SEQ ID NO: 7, SEQ ID NO: 9, SEQ ID NO: 11, SEQ ID NO: 13, SEQ ID NO: 15 or SEQ ID NO: 17 under high-stringency conditions. In still another embodiment, the high-stringency conditions are 7% sodium dodecyl sulfate (SDS), 0.5 M NaP$_{O4}$, 1 mM EDTA at 50° C. with washing in 0.1×SSC, 0.1% SDS at 65° C. In a further embodiment, the Vip3A protein is selected from the group consisting of Vip3Aa1 (AAC37036), Vip3Aa2 (AAC37037), Vip3Aa3 (U.S. Pat. No. 6,137,033), Vip3Aa4 (AAR81079), Vip3Aa5 (AAR81080), Vip3Aa6 (AAR81081), Vip3Aa7 (AAK95326), Vip3Aa8 (AAK97481), Vip3Aa9 (CAA76665), Vip3Aa10 (AAN60738), Vip3Aa11 (AAR36859), Vip3Aa12 (AAM22456), Vip3Aa13 (AAL69542), Vip3Aa14 (AAQ12340), Vip3Aa15 (AAP51131), Vip3Aa16 (AAW65132), Vip3Aa17 (U.S. Pat. No. 6,603,063), Vip3Aa18 (AAX49395), Vip3Aa19 (DQ241674), Vip3Aa19 (DQ539887), Vip3Aa20 (DQ539888), Vip3Aa21 (ABD84410), Vip3Aa22 (AAY41427), Vip3Aa23 (AAY41428), Vip3Aa24 (BI 880913), Vip3Aa25 (EF608501), Vip3Aa26 (EU294496), Vip3Aa27 (EU332167), Vip3Aa28 (FJ494817), Vip3Aa29 (FJ626674), Vip3Aa30 (FJ626675), Vip3Aa31 (FJ626676), Vip3Aa32 (FJ626677), Vip3Aa33 (GU073128), Vip3Aa34 (GU073129), Vip3Aa35 (GU733921), Vip3Aa36 (GU951510), Vip3Aa37 (HM132041), Vip3Aa38 (HM117632), Vip3Aa39 (HM117631), Vip3Aa40 (HM132042), Vip3Aa41 (HM132043), Vip3Aa42 (HQ587048), Vip3Aa43 (HQ594534), Vip3Aa44 (HQ650163), Vip3Ab1 (AAR40284), Vip3Ab2 (AAY88247), Vip3Ac1 (US Patent Application Publication 20040128716), Vip3Ad1 (US Patent Application Publication 20040128716), Vip3Ad2 (CAI43276), Vip3Ae1 (CAI43277), Vip3Af1 (CAI43275), Vip3Af2 (ADN08753), Vip3Af3 (HM117634), Vip3Ag1 (ADN08758), Vip3Ag2 (FJ556803), Vip3Ag3 (HM117633), Vip3Ag4 (HQ414237), Vip3Ag5 (HQ542193), and Vip3Ah1 (DQ832323). In still a further embodiment, the Vip3A protein comprises SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16, or a nematode-active homologue thereof having at least 80%, 81%, 82%, 83%, 84%, 85%, 86%, 87%, 88%, 89%, 90%, 91%, 92%, 93%, 94%, 95%, 96%, 97%, 98% or 99% identity with SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16. In another embodiment, the Vip3A protein comprises SEQ ID NO: 1 or a nematode-active homologue having at least 80%, 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1.

In another embodiment, the agricultural carrier is a transgenic plant or plant part. In yet another embodiment, the transgenic plant or plant part is a soybean plant or plant part.

In one embodiment, the invention encompasses a method of producing a nematode-resistant plant or plant part comprising introducing a nucleic acid molecule encoding a Vip3 protein into the plant or plant part thereby producing a transgenic plant or plant part, wherein the nucleic acid molecule causes the expression of the Vip3 protein in an amount that makes the transgenic plant or plant part resistant to nematodes.

In still another embodiment, the invention encompasses a method of reducing nematode cyst development on roots of a plant infected by a nematode, comprising introducing into cells of the plant a nucleic acid molecule capable of directing the expression of a Vip3 protein, thereby reducing nematode cyst development on roots of the plant.

The invention also encompasses a method for controlling or preventing nematode growth comprising providing a nematode pest with plant material comprising a heterologous nucleic acid molecule capable of directing expression of a Vip3 protein, wherein the plant material inhibits a nematode biological activity. In another embodiment, the biological activity is an ability to produce cysts on roots of plants. In yet another embodiment, the plant material is a soybean plant or plant part.

In another embodiment, the invention encompasses a method of suppressing the growth of a plant-pathogenic nematode population in a location capable of supporting said growth comprising growing in the location a population of transgenic soybean plants comprising a heterologous nucleic acid molecule capable of directing expression of a Vip3 protein, wherein the plant-pathogenic nematode population is suppressed.

The present invention also encompasses recombinant vectors and expression cassettes comprising the vip3 nucleic acid sequences of the invention. In such vectors, the nucleic acid sequences are preferably comprised in expression cassettes comprising regulatory elements for expression of the vip3 nucleotide sequences in a transgenic host cell capable of expressing the nucleotide sequences. Such regulatory elements usually comprise promoter and termination signals and preferably also comprise elements allowing efficient translation of polypeptides encoded by the nucleic acid sequences of the present invention. Vectors comprising the nucleic acid sequences are usually capable of replication in particular host cells, preferably as extrachromosomal molecules, and are therefore used to amplify the nucleic acid sequences of this invention in the host cells. In one embodiment, host cells for such vectors are microorganisms, such as bacteria, in particular *E. coli*. In another embodiment, host cells for such recombinant vectors are endophytes or epiphytes. One example of a host cell for such vectors is a eukaryotic cell, such as a plant cell. Such plant cells may be soybean cells or maize cells. In another embodiment, such vectors are viral vectors and are used for replication of the nucleotide sequences in particular host cells, e.g. insect cells or plant cells. Recombinant vectors are also used for transformation of the nucleotide sequences of this invention into transgenic host cells, whereby the nucleotide sequences are stably integrated into the DNA of such transgenic host cells. In one, such transgenic host cells are prokaryotic cells. In another embodiment, such transgenic host cells are eukaryotic cells, such as yeast cells, insect cells, or plant cells. In still another embodiment, the transgenic host cells are plant cells, such as soybean cells or maize cells.

The present invention further encompasses an expression cassette comprising an actin promoter operably linked to a vip3 coding sequence operably linked to a terminator, wherein the expression cassette functions in a transgenic plant to drive expression of a Vip3 protein at a nematode-controlling effective amount. In another embodiment, the actin promoter is an actin2 promoter and the terminator is a NOS terminator. In yet another embodiment, the vip3 coding sequence comprises a nucleotide sequence whose complement hybridizes to SEQ ID NO: 2, SEQ ID NO: 4, SEQ ID NO: 5, SEQ ID NO: 7, SEQ ID NO: 9, SEQ ID NO: 11, SEQ ID NO: 13, SEQ ID NO: 15 or SEQ ID NO: 17 under high-stringency conditions. In a further embodiment, the high-stringency conditions are 7% sodium dodecyl sulfate (SDS), 0.5 M $NaP_{O4}$, 1 mM EDTA at 50° C. with washing in 0.1×SSC, 0.1% SDS at 65° C. In another embodiment, the Vip3 protein comprises SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16, or a nematode-active homologue thereof having at least 80%, 81%, 82%, 83%, 84%, 85%, 86%, 87%, 88%, 89%, 90%, 91%, 92%, 93%, 94%, 95%, 96%, 97%, 98% or 99% identity with SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16. In another embodiment, the Vip3A protein comprises SEQ ID NO: 1 or a nematode-active homologue having at least 80%, 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 1.

In further embodiments, the vip3 nucleotide sequences of the invention can be modified by incorporation of random mutations in a technique known as in vitro recombination or DNA shuffling to increase nematode activity for example. This technique is described in Stemmer et al., Nature 370:389-391 (1994) and U.S. Pat. No. 5,605,793, which are incorporated herein by reference. Millions of mutant copies of a nucleotide sequence are produced based on an original nucleotide sequence of this invention and variants with improved properties, such as increased nematicidal activity, enhanced stability, or different specificity or range of target nematode pests are recovered. The method encompasses forming a mutagenized double-stranded polynucleotide from a template double-stranded polynucleotide comprising a nucleotide sequence of this invention, wherein the template double-stranded polynucleotide has been cleaved into double-stranded-random fragments of a desired size, and comprises the steps of adding to the resultant population of double-stranded random fragments one or more single or double-stranded oligonucleotides, wherein said oligonucleotides comprise an area of identity and an area of heterology to the double-stranded template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. In a preferred embodiment, the concentration of a single species of double-stranded random fragment in the population of double-stranded random fragments is less than 1% by weight of the total DNA. In a further embodiment, the template double-stranded polynucleotide comprises at least about 100 species of polynucleotides. In another preferred embodiment, the size of the double-stranded random fragments is from about 5 by to 5 kb. In another embodiment, the fourth step of the method comprises repeating the second and the third steps for at least 10 cycles.

In another embodiment, at least one of the vip3 nucleotide sequences of the invention is inserted into an appropriate expression cassette, comprising a promoter and termination signals. Expression of the nucleotide sequence is constitutive, or an inducible promoter responding to various types of stimuli to initiate transcription is used. In a preferred embodiment, the cell in which the toxin is expressed is a microorganism, such as a virus, a bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes,*

*Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleotide sequences for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. In:Industrial Microorganisms:Basic and Applied Molecular Genetics, Eds. Baltz et al., American Society for Microbiology, Washington (1993)). Alternate systems for overexpression rely for example, on yeast vectors and include the use of *Pichia, Saccharomyces* and *Kluyveromyces* (Sreekrishna, In:Industrial microorganisms:basic and applied molecular genetics, Baltz, Hegeman, and Skatrud eds., American Society for Microbiology, Washington (1993); Dequin & Bane, Biotechnology L2:173-177 (1994); van den Berg et al., Biotechnology 8:135-139 (1990)).

In one embodiment, at least one Vip3 protein of the invention is expressed in a higher organism, e.g., a plant. In this case, transgenic plants expressing effective amounts of the toxins protect themselves from nematode pests. When the nematode starts feeding on such a transgenic plant, it also ingests the expressed Vip3 toxin. This may deter the nematode from further feeding in the plant tissue, may harm or kill the nematode or may reduce the nematodes ability to reproduce. A nucleotide sequence of the present invention is inserted into an expression cassette, which is then preferably stably integrated in the genome of the plant. Plants transformed in accordance with the invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of the invention is expressed in transgenic plants, thus causing the biosynthesis of the corresponding toxin in the transgenic plants. In this way, transgenic plants with enhanced resistance to nematodes are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods known in the art.

In one embodiment of the invention synthetic genes are made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid can be derived, for example, from known gene sequences from maize. Maize codon usage for 28 genes from maize plants is found in Murray et al., Nucleic Acids Research 17:477-498 (1989), the disclosure of which is incorporated herein by reference. A specifically exemplified synthetic sequence of the invention made with maize optimized codons is set forth in SEQ ID NO:2.

In this manner, the nucleotide sequences can be optimized for expression in any plant. It is recognized that all or any part of the gene sequence may be optimized or synthetic. That is, synthetic or partially optimized sequences may also be used.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

The vip3 toxin genes of the invention, either as their native sequence or as optimized synthetic sequences as described above, can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. The choice of promoter will vary depending on the temporal and spatial requirements for expression. Thus, expression of the nucleotide sequences encoding Vip3 proteins of the invention in leaves, in stalks or stems, in ears, in inflorescences (e.g. spikes, panicles, cobs, etc.), in roots, and/or seedlings can be achieved, but particularly preferred for control of nematodes is expression in roots. In many cases, however, protection against more than one type of nematode pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences of the invention in the desired cell.

Constitutive promoters include for example the Actin 2 promoter (An et al. (1996) Plant J 10(1):107-21). Additionally, a promoter useful in the present invention could be derived from any one of several of the actin genes, which are expressed in most cell types. The promoter expression cassettes described by McElroy et al. (Mol. Gen. Genet. 231: 150-160 (1991)) can be modified for the expression of the novel toxin gene and are particularly suitable for use in monocotyledonous hosts.

Yet another constitutive promoter is derived from ubiquitin, which is another gene product known to accumulate in many cell types. A ubiquitin promoter has been cloned from several species for use in transgenic plants, for example, sunflower (Binet et al., 1991. Plant Science 79: 87-94), maize (Christensen et al., 1989. Plant Molec. Biol. 12: 619-632), and *arabidopsis* (Norris et al. 1993. Plant Molec. Biol. 21:895-906). The maize ubiquitin promoter has been developed in transgenic monocot systems and its sequence and vectors constructed for monocot transformation are disclosed in the patent publication EP 0 342 926. The ubiquitin promoter is suitable for the expression of the novel toxin gene in transgenic plants, especially monocotyledons.

Tissue-specific or tissue-preferential promoters useful for the expression of the novel toxin genes of the invention in plants, particularly maize, are those that direct expression in root, pith, leaf or pollen. Such promoters are disclosed in WO 93/07278, herein incorporated by reference in its entirety. Other tissue specific promoters useful in the present invention include the cotton rubisco promoter disclosed in U.S. Pat. No. 6,040,504; the rice sucrose synthase promoter disclosed in U.S. Pat. No. 5,604,121; and the cestrum yellow leaf curling virus promoter disclosed in WO 01/73087, all incorporated by reference. Chemically inducible promoters useful for directing the expression of the novel toxin gene in plants are disclosed in U.S. Pat. No. 5,614,395 herein incorporated by reference in its entirety.

The nucleotide sequences of the invention can also be expressed under the regulation of promoters that are chemically regulated. This enables the Vip3 toxins to be synthesized only when the crop plants are treated with the inducing chemicals. One example of a promoter for chemical induction is the PR-1a promoter detailed in the U.S. Pat. No. 5,614,395, incorporated herein by reference.

Another category of promoters useful in the invention is that which is wound inducible. Numerous promoters have been described which are expressed at wound sites and also at the sites of phytopathogen infection. Ideally, such a promoter should only be active locally at the sites of infection, and in this way the insecticidal toxins only accumulate in cells that need to synthesize the insecticidal toxins to kill the invading insect pest. Examples of promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Tissue specific expression patterns include green tissue specific, root specific, stem specific, and flower specific. Promoters suitable for expression in green tissue include many that regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12:579-589 (1989)). A preferred promoter for root specific expression is that described by de Framond (FEBS 290:103-106 (1991); EP 0 452 269 to Ciba-Geigy). A preferred stem specific promoter is that described in U.S. Pat. No. 5,625,136 (to Ciba-Geigy) and which drives expression of the maize trpA gene.

Further embodiments of the invention are transgenic plants expressing the nucleotide sequences in a wound-inducible or nematode-inducible manner.

In addition to the selection of a suitable promoter, constructions for expression of an insecticidal toxin in plants require an appropriate transcription terminator to be attached downstream of the heterologous nucleotide sequence. Several such terminators are available and known in the art (e.g. tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be useful to target expression of the nucleotide sequences of the invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well known in the art.

Numerous transformation vectors available for plant transformation are known to those of ordinary skill in the plant transformation art, and the nucleic acid molecules of the invention can be used in conjunction with any such vectors. The selection of vector will depend upon the preferred transformation technique and the target plant species for transformation. For certain target species, different antibiotic or herbicide selection markers may be preferred. Selection markers used routinely in transformation include the nptII gene, which confers resistance to kanamycin and related antibiotics (Messing & Vierra., 1982. Gene 19: 259-268; and Bevan et al., 1983. Nature 304:184-187), the bar gene, which confers resistance to the herbicide phosphinothricin (White et al., 1990. Nucl. Acids Res 18: 1062, and Spencer et al., 1990. Theor. Appl. Genet 79: 625-631), the hph gene, which confers resistance to the antibiotic hygromycin (Blochinger & Diggelmann, Mol Cell Biol 4: 2929-2931), and the dhfr gene, which confers resistance to methatrexate (Bourouis et al., 1983. EMBO J. 2(7): 1099-1104), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994,629). The choice of selectable marker is not, however, critical to the invention.

In another embodiment, a nucleotide sequence of the invention is directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid-targeting vector and transformed into the plastid genome of a desired plant host. Plants homoplastic for plastid genomes containing a nucleotide sequence of the present invention are obtained, and are preferentially capable of high expression of the nucleotide sequence.

It will be apparent to the skilled person that the Vip3 proteins of the invention can be used in combination with other nematicidal agents such as proteins, chemicals, other natural products and the like. Non-limiting examples of such chemicals and natural products include abamectin, carbamate nematicides selected from aldicarb, carbofuran, carbosulfan, oxamyl, aldoxycarb, ethoprop benomyl, and alanycarb; organophosphorus nematicides selected from phenamiphos, fenamiphos, fensulfothion, terbufos, fosthiazate, phosphocarb, dichlofenthion, isamidofos, fosthietan, isazofos, ethoprophos, cadusafos, chlorpyrifos, heterophos, isamidofos, mecarphon, phorate, thionazin, triazophos, diamidafos, and phosphamidon; methyl bromide, methyl iodide, carbon disulfide, 1,3-dichloropropene, chloropicrin, cytokinins, dazomet, DCIP, ethylene dibromide, GY-81, metam, methyl isocyanate, *myrothecium verrucaria* composition, and flupyrazofos, benchlothiaz, [2-cyanoimino-3-ethylimidazolidin-1-yl]phosphonothioic acid O-ethyl S-propyl ester.

Avermectins and derivatives of avermectins for use in the invention are known. Abamectin and abamectin seed treatment formulations for nematode control that are particularly useful in the invention are disclosed, e.g., in U.S. Pat. No. 6,875,727. Agrochemically compatible salts are, for example, acid addition salts of inorganic and organic acids, in particular of hydrochloric acid, hydrobromic acid, sulfuric acid, nitric acid, perchloric acid, phosphoric acid, formic acid, acetic acid, tri-fluoroacetic acid, oxalic acid, malonic acid, toluenesulfonic acid or benzoic acid. Examples of formulations of avermectin compounds that can be used in the method according to the invention, i.e., solutions, granules, dusts, sprayable powders, emulsion concentrates, coated granules and suspension concentrates, have been described, e.g., in EP-A-580 553.

Derivatives of avermectin or abamectin can be obtained via conventional chemical syntheses. For example, in some embodiments emamectin, which is 4"-De-oxy-4"-epi-N-methylamino avermectin B.sub.1b/B.sub.1a known from U.S. Pat. No. 4,874,749, can be used. Agrochemically useful salts of emamectin are additionally described, e.g., in U.S. Pat. No. 5,288,710.

The amount of a nematicide present on (or adhered to) the seed varies, for example, according to type of crop, and type of plant propagation material. However, the amount is such that the at least one nematicide is an effective amount to provide the desired enhanced action and can be determined by routine experimentation and field trials. In the event the nematicide is abamectin, the amount of active abamectin ingredient present in the seed coating is in the range of from 0.002 to 1.2 mg/seed, typically at least 0.1 mg/seed, often at least 0.2 mg/seed. Frequently, the abamectin is present at a level of 0.3 mg or more per seed.

Bacterial parasites can also be used as nematode antagonistic biocontrol agents. These include, e.g., *Pasteuria* species, e.g., *P. penetrans*, *P. nishizawae*, *P. thornei*, *Candidatus Pasteuria* usgae sp. nov., *Myrothecium verrucaria*, *Candidatus Pasteuria* sp. strain HG, and other species. These parasites can attach to the cuticle of nematodes.

The nematicidal Vip3 toxins of the invention can be used in combination with Bt Cry toxins or other pesticidal principles to increase pest target range. Such Bt Cry toxins include for example Cry1, Cry 5, Cry6, Cry11, Cry12, Cry13, Cry14, Cry21 and Cry22. Furthermore, the use of the nematicidal Vip3 toxins of the invention in combination with Bt δ-endotoxins or other pesticidal principles of a distinct nature has particular utility for the prevention and/or management of nematode resistance.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual,* 3d Ed., Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1

Construction of Expression Cassettes

A vip3A coding sequence (SEQ ID NO: 2) was cloned into a act2:vip3A:tNOS expression cassette. The expression cassette with the vip3A coding sequence was then cloned into a binary vector to create the vector pKS214 (SEQ ID NO: 18).

Example 2

Expression Vip3 in Transgenic Soybean Roots

The pKS214 binary expression vector containing a vip3A gene and an empty vector (without vip3A coding sequence) were transformed into soybean roots to test pKS214's ability to reduce soybean cyst nematode (SCN) cysts as transgenes. Soybean cultivar Williams 82 was used as the germplasm for the hairy root transformation. Seeds of soybean seeds were germinated on 1% agar containing 0.5% sucrose in Petri dishes at 27° C. for 5 days. The cotyledons were then cut off the seedlings, and the wounded surface was inoculated with cultures of the *Agrobacterium rhizogenes* carrying the binary vector. The cotyledons were placed on 1% agar for 6 days and then transferred onto selection media. In about two weeks, independent transgenic hairy root events induced from the cotyledons were harvested and transferred onto culture media, and cultured in the darkness at 27° C. Narayanan et al. indicated that SCN resistance phenotypes in the whole plant were preserved in transgenic hairy roots, therefore transgenic hairy root system is useful for evaluating candidate SCN resistance genes. Narayanan et al. (1999) *Crop Science* 39, 1680-1686.

Approximately two weeks after transfer onto the culture plates, the transformed hairy roots were inoculated with surface-sterilized J2 stage soybean cyst nematodes (SCN J2) and the roots were grown in darkness at 27° C., which allowed cyst formation on the hairy root events. One month after nematode inoculation, the number of cysts was determined for both the roots expressing Vip3 protein and the roots expressing the empty vector (as a negative control).

The experiment was repeated five (5) times. Table 1 and FIG. 1 show the summary of the comparison of mean cyst number. ANOVA test indicated that the average number of cysts formed on the transgenic soybean roots expressing Vip3 protein is significantly lower than on the transgenic soybean roots comprising the empty vector control ($p<0.05$).

TABLE 1

In vivo transgenic root-SCN assay

| Plasmid ID | Gene of Interest | Avg. Cysts | n | Standard error |
|---|---|---|---|---|
| Empty Vector | None (Negative Control) | 60 | 5 | 3.8 |
| pKS104 (SEQ ID NO: 16) | vip3Aa20 | 28 | 5 | 1.1 |

Example 2

Production of Transgenic Soybean Expressing Vip3 Protein

Transformation of soybean to produce transgenic soybean plants is accomplished using immature seed targets of variety Williams 82 via *A. tumefaciens*-mediated transformation. Explant materials and media recipes were essentially as described in Hwang et al. (PCT International Publication No. WO 08/112,044) and Que et al. (PCT International Publication No. WO 08/112,267), with some variations as noted below. Using this method, genetic elements within the left and right border regions of the transformation plasmid are efficiently transferred and integrated into the genome of the plant cell, while genetic elements outside these border regions are generally not transferred.

Maturing soybean pods are harvested from greenhouse-grown plants, sterilized with diluted bleach solution, and rinsed with sterile water Immature seeds are then excised from seedpods and rinsed briefly with sterile water. Explants are prepared from sterilized immature seeds as described in Hwang et al. (PCT International Publication No. WO 08/112,044) and infected with *A. tumefaciens* strain EHA101 harboring the transformation binary vector 18963 and allowed to incubate for an additional 30 to 240 minutes. Excess *A. tumefaciens* suspension is removed by aspiration and the explants are moved to plates containing a non-selective co-culture medium. The explants are co-cultured with the remaining *A. tumefaciens* at 23° C. for 4 days in the dark and then transferred to recovery and regeneration medium supplemented with an antibiotics mixture consisting of ticarcillin (75 mg/L), cefotaxime (75 mg/L) and vancomycin (75 mg/L) where they are incubated in the dark for seven days.

The explants are then transferred to regeneration medium containing hygromycin B (3 to 6 mg/L) and a mixture of antibiotics consisting of ticarcillin (75 mg/L), cefotaxime (75 mg/L) and vancomycin (75 mg/L) to inhibit and kill *A. tumefaciens*. Shoot elongation and regeneration is carried out in elongation media containing 2-4 mg/L of hygromycin B. The hygromycin phosphor-transferase (HPT) gene was used as a selectable marker during the transformation process. Regenerated plantlets are transplanted in soil as described (PCT International Publication No. WO 08/112, 267) and tested for the presence of HPT and CMP promoter sequences using TaqMan PCR analyses. Ingham et al. (2001) *Biotech* 31, 132-140. This screen allows for the selection of transgenic events that carry the T-DNA and are free of vector DNA. Plants positive for HPT gene and CMP sequences and negative for the spectinomycin (spec) gene are transferred to the greenhouse for analysis of miRNA expression and seed setting.

When the roots are about 2-3 inches, they are then transplanted into 1-gallon pots using Fafard #3 soil and 30 grams of incorporated Osmocote Plus 15-9-12. They are watered in thoroughly and placed in the cubicle under florescent lighting set to a 16-hour day. The temperatures are 85° F. (29.4° C.) during the day and 70° F. (21° C.) at night. Plants are watered once daily.

The plants remain in the cubicle until secondary Taqman sampling has been performed, typically 1-2 weeks. The plants are then placed on an automatic drip watering system and watered twice daily. A cage is placed over the plant, and it may be pruned very lightly if needed. The lighting is a combination of Metal Halide and Sodium Vapor fixtures with 400- and 1000-watt bulbs with a 10-hour day period. The outside wall is darkened to keep out light that would extend the day length. Temperatures are set at 79° F. (26° C.) during the day and 70° F. (21° C.) at night. The humidity is ambient.

The plants are maintained in this manner until pods reach maturity, approximately 100 days based on the date of the Taqman selection. The pods are then harvested, placed in a paper bag, air-dried for 2-days, and then machine dried at 80° F. (27° C.) for 2-additional days. The pods are shelled and the T1 seeds are harvested and stored at 4° C. until further testing.

Example 3

Analysis of Transgenic Soybean Plants

Soybean plants were transformed with one of three binary vectors, 1) vector 19993 comprising an expression cassette with an *Arabidopsis* actin 2 promoter operatively linked to a vip3A coding sequence which is operatively linked to a nopaline synthetase terminator (prAct2:vip3A:tNOS); or 2) vector 20048 comprising an expression cassette with a *Medicago truncatula* Mt51186 promoter operatively linked to a vip3A coding sequence which is operatively linked a nopaline synthetase terminator (prMt51186:vip3A:tNOS); or 3) a vector comprising an expression cassette with a cestrum virus promoter operatively linked to a vip3A coding sequence which is operatively linked a nopaline synthetase terminator (cmp:vip3A:tNOS). T1 transgenic soybean plants and control plants are inoculated with J2-stage soybean cyst nematodes (SCN J2). Briefly, 1-3 week old seedlings of the transgenic T1 generation soybean that are either homozygous (Hom) or heterozygous (Het) for the vip3 gene or null segregants (i.e. do not comprise a vip3 gene; Null) were grown in germination pouches and inoculated with a suspension of J2 stage soybean cyst nematodes at the level of 750 J2 per plant. Approximately one month after nematode inoculation, the number of cysts is determined for the transgenic plants comprising the vip3 expression cassette and for the null segregants from the same T0 parents.

Results shown in Table 2 demonstrate that transgenic T1 soybean expressing Vip3 protein have reduced number of SCN cysts compared to the null segregant (negative control). Transformed plants comprising the cmp:vip3A:nos expression cassette did not have a reduced number of cysts compared to the null segregant.

TABLE 2

Efficacy of transgenic soybean expressing Vip3 against SCN

| Binary Vector | Promoter | Soybean Event | Zygosity | N | No. of Cysts | Standard Error |
|---|---|---|---|---|---|---|
| 19993 | Act 2 | 9358 | Het | 6 | 82.0 | 9.3 |
| | | | Hom | 3 | 79.3 | 11.1 |
| | | | NULL | 3 | 99.0 | 12.3 |
| | | 9363 | Het | 1 | 120.0 | |
| | | | Hom | 22 | 115.0 | 9.8 |
| | | | NULL | 5 | 137.0 | 6.4 |
| | | 0052 | Het | 7 | 91.9 | 8.0 |
| | | | Hom | 12 | 86.5 | 6.0 |
| | | | NULL | 10 | 120.5 | 10.4 |
| | | 2600 | Het | 16 | 110.7 | 6.9 |
| | | | Hom | 6 | 82.7 | 18.1 |
| | | | NULL | 5 | 117.0 | 12.0 |
| 20048 | Mt51186 | 6861 | Het | 5 | 82.2 | 15.6 |
| | | | HOM | 3 | 123.3 | 16.6 |
| | | | NULL | 4 | 138.8 | 15.5 |

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

It should be understood that the examples and embodiments described herein are for illustrative purposes only and that various modifications or changes in light thereof will be suggested to persons skilled in the art and are to be included within the spirit and purview of this application and the scope of the appended claims.

The invention claimed is:

1. A method of controlling a *Heterodera* pest, comprising contacting the *Heterodera* pest with a transgenic soybean plant or soybean plant part thereof comprising a heterologous nucleic acid molecule that directs expression of a Vip3A protein comprising SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16, or a sequence having at least 95% sequence identity with SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16 in the transgenic soybean plant or soybean plant part, wherein the transgenic soybean plant or soybean plant part controls the nematode pest compared to a soybean plant or soybean plant part of the same type that does not express the Vip3A protein comprising SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16, or a sequence having at least 95% sequence identity with SEQ ID NO: 1, SEQ ID NO: 3, SEQ ID NO: 6, SEQ ID NO: 8, SEQ ID NO: 10, SEQ ID NO: 12, SEQ ID NO: 14 or SEQ ID NO: 16.

2. The method of claim 1, wherein the *Heterodera* pest is *Heterodera glycines*.

3. The method of claim 1, wherein the transgenic plant further comprises or expresses at least one additional pesticidal agent selected from the group consisting of a patatin, a lectin, a *Bacillus thuringiensis* insecticidal protein, a *Bacillus thuringiensis* nematicidal protein, a *Xenorhabdus* insecticidal protein, a *Photorhabdus* insecticidal protein, a *Bacillus laterosporous* insecticidal protein, and a *Bacillus sphearicus* insecticidal protein.

4. The method of claim 3, wherein the *Bacillus thuringiensis* nematicidal protein is selected from the group consisting of Cry1, Cry3, Cry11, Cry12, Cry13, Cry14, Cry21, and Cry22.

5. A method of producing a soybean plant protected against nematode infestation, comprising:
   a. transforming a soybean plant cell with a nucleic acid molecule comprising a plant promoter and encoding a Vip3A protein comprising SEQ ID NO: 1
   b. regenerating a transformed soybean plant from the soybean plant cell.

6. A method of producing a soybean plant protected against nematode infestation, comprising:
   a. crossing a first parent soybean plant with a second parent soybean plant, wherein said first or second parent soybean plant comprises a heterologous nucleic acid molecule comprising a plant promoter and encoding a Vip3A protein comprising SEQ ID NO: 1, thereby producing a plurality of progeny plants;
   b. selecting from the plurality of progeny plants, a transgenic plant that is protected against nematode infestation.

7. A method of controlling *Heterodera glycines* comprising providing a transgenic soybean plant or plant part comprising an expression cassette having SEQ ID NO: 2 operably linked to a plant promoter capable of driving expression of an encoded Vip3A protein comprising SEQ ID NO: 1 to levels sufficient to inhibit nematodes, wherein the proliferation of *Heterodera glycines* cysts on said plant or plant part is reduced compared to *Heterodera glycines* cysts on a soybean plant or plant part not expressing the Vip3A protein.

8. A method of increasing the vigor or yield in a transgenic soybean plant exposed to a population of nematodes comprising:
   a. introgressing a transgenic soybean event into a soybean plant resulting in a transgenic soybean plant, wherein the transgenic soybean event comprises a heterologous nucleic acid molecule comprising a plant promoter and encoding a Vip3A protein comprising SEQ ID NO: 1, wherein the Vip3A protein confers upon the transgenic soybean event resistance to nematodes; and
   b. growing the transgenic soybean plant or progeny thereof at a location where nematode infestation is yield limiting to a soybean plant not comprising the heterologous nucleic acid molecule encoding the Vip3A protein, whereby the transgenic soybean plant has increased vigor or yield compared to the control plant.

9. A method of producing a nematode-resistant soybean plant, comprising introducing a nucleic acid molecule comprising a plant promoter and encoding a Vip3A protein comprising SEQ ID NO: 1 into the soybean plant thereby producing a transgenic soybean plant, wherein the nucleic acid molecule causes the expression of the Vip3A protein in an amount that makes the transgenic soybean plant resistant to nematodes.

10. A method of reducing nematode cyst development on roots of a soybean plant infected by a nematode, comprising introducing into cells of the soybean plant a nucleic acid molecule comprising a plant promoter and capable of directing the expression of a Vip3A protein comprising SEQ ID NO: 1, thereby reducing nematode cyst development on roots of the soybean plant.

11. A method for controlling or preventing nematode growth comprising providing a nematode pest with soybean plant material comprising a heterologous nucleic acid molecule comprising a plant promoter and capable of directing expression of a Vip3A protein comprising SEQ ID NO: 1, wherein said soybean plant inhibits a nematode biological activity.

12. A method of improving soybean yield, comprising:
   a. introducing into a soybean plant a nucleic acid molecule comprising a plant promoter and capable of directing expression of a Vip3A protein comprising SEQ ID NO: 1; and
   b. cultivating a plurality of transgenic seeds from the plant of step (a), resulting in a plurality of transgenic plants having enhanced resistance to nematode infestation, thereby improving soybean yield.

\* \* \* \* \*